US006015691A

United States Patent [19]

Walker et al.

[11] Patent Number: 6,015,691

[45] Date of Patent: Jan. 18, 2000

[54] **IMMUNODOMINANT 120 KDA SURFACE-EXPOSED ADHESION PROTEIN GENES OF *EHRLICHIA CHAFFEENSIS***

[75] Inventors: David H. Walker; Xue-Jie Yu, both of Galveston, Tex.

[73] Assignee: Research Development Foundation, Carson, Nev.

[21] Appl. No.: 08/656,034

[22] Filed: May 31, 1996

[51] Int. Cl.[7] .......................... C12N 15/00; C12N 15/31; C07K 14/00; A61K 39/02

[52] U.S. Cl. .................... 435/69.1; 435/69.7; 435/252.3; 435/320.1; 530/350; 530/387.1; 536/23.1; 536/23.5; 536/23.4; 536/24.33; 536/24.31; 536/24.32; 536/24.3; 536/24.5; 424/234.1

[58] Field of Search ................................ 536/23.1, 23.5, 536/23.4, 24.33, 24.31, 24.32, 24.3, 24.5; 530/350, 387.1; 435/320.1, 252.3, 69.1, 69.7; 424/234.1

[56] References Cited

FOREIGN PATENT DOCUMENTS 8900163 1/1989 WIPO .
9218113 10/1992 WIPO .

OTHER PUBLICATIONS

Sumner et al., "*Ehrlichia Chaffeensis* Expresses an Immunoreactive Protein Homologous to the *Escherichia Coli* GroEL Protein," *Infect Immun,* 61:3536–3539, 1993.

Tal and Shannahan, "Ehrlichiosis Presenting as a Life–Threatening Illness," *Am J Med,* 98:318–319, 1995.

Uhaa et al., "A Case of Human Ehrlichiosis Acquired in Mali: Clinical and Laboratory Findings," *Am J Trop Med Hyg,* 46:161–164, 1992.

Vanek et al., "Human Ehrlichiosis Causing Left Ventricular Dilatation and Dysfunction," *Clin Infect Dis,* 22:386–387, 1996.

Van Vliet et al., "Phylogenetic Position of *Cowdria Ruminantium* (Rickettsiales) Determined by Analysis of Amplified 16S Ribosomal DNA Sequences," *Int J Syst Bacteriol,* 42:494–498, 1992.

Walker et al., "Emergence of the Ehrlichiosis as Human Health problems," *Emerg Infect Dis,* 2:18–29, 1996.

Walker, "Human Ehrlichiosis: More Trouble from Ticks," *Hosp Pract,* 31:47–57, 1996.

Wellman et al., "A Macrophage–MonocyteCell Line from a Dog with Malignant Histiocytosis," *In Vitro Cellular & Developmental Biology,* 24(3):223–229, 1988.

Wen et al., "*Ehrlichia Muris* Sp. Nov., Identified on the Basis of 16S rRNA Base Sequences and Serological, Morphological, and Biological Characteristics," *Int J Syst Bacteriol,* 45:250–254, 1995.

Yevich et al., "Seroepidemiology of Infections Due to Spotted Fever Group Rickettsiae and Ehrlichia Species in Military Personnel Exposed in Areas of the United States Where Such Infections are Endemic," *J Infect Dis,* 171:1266–1273, 1995.

Yu et a., "Detection of *Ehrlichia Chaffeensis* in Human Ti9ssue by Using a Species–Specific Monoclonal Antibody," *J Clin Microbiol,* 31:3284–3288, Dec. 1993.

Anderson et al., "*Amblyomma Americanum:* A Potential Vector of Human Ehrlichiosis," *Am J Trop Med Hyg,* 49:239–244, 1993.

Anderson et al., "Detection of the Etiologic Agent of Human Ehrlichiosis by Polymerase Chain Reaction," *J Clin Microbiol,* 30:775–780, 1992.

Anderson et al., "*Ehrlichia Ewingii* Sp. Nov., The Etiologic Agent of Canine Granulocytic Ehrlichiosis," *Int. J Syst Bacteriol,* 42:299–302, 1992.

Barenfanger et al., "Identifying Human Ehrlichiosis," *Lab Med,* 27:372–374, 1996.

Brouqui et al., "Antigenic CharacterizationofEhrlichiae: Protein Immunoblotting of *Ehrlichia Canis, Ehrlichia Sennetsu,* and *Ehrlichia Risticii,* " *Journal of Clinical Microbiology,* 30(5):1062–1066, May 1992.

Brouqui et al., "Serologic Evidence for Human Ehrlichiosis in Africa," *Eur J Epidemiol,* 10:695–698, 1994.

Brouqui et al., "Serologic Diagnosis of Human Monocytic Ehrlichiosis by Immunoblot Analysis," *Clin Diagn Lab Immunol,* 1:645–649, 1994.

Chen et al., "Analysis and Ultrastructural Localization of *Ehrlichia Chaffeensis* Proteins with Monoclonal Antibodies," *Am J Trop Med,* 54:405–412, 1996.

Chen et al., "Identification of the Antigenic Constituents of *Ehrlichia Chaffeensis," Am J Trop Med Hyg,* 50(1):52–58, 1994.

Dawson et al., "Diagnosis of Human Ehrlichiosis with the Indirect Fluorescent Antibody Test: Kinetics and Specificity," *J Infect Dis,* 162:91–95, 1990.

Dawson et al., "The Interface Between Research and the Diagnosis of an Emerging Tick–Borne disease, Human Ehrlichia due to *Ehrlichia Chaffeensis," Arch Intern Med,* 156:137–142, 1996.

Dawson et al., "Isolation and Characterization of an Ehrlichia Sp. from a Patient Diagnosed with Human Ehrlichiosis," *J Clin Microbiol,* 29:2741–2745, 1991.

Dawson and Ewing, "Susceptibility of Dogs to Infection with *Ehrlichia Chaffeensis,* Causative Agent of Human Ehrlichiosis," *Am J Vet Res,* 53:1322–1327, 1992.

(List continued on next page.)

*Primary Examiner*—Paula K. Hutzell
*Assistant Examiner*—Khalzd Masood
*Attorney, Agent, or Firm*—Arnold White & Durkee

[57] ABSTRACT

Disclosed is an isolated gene encoding a 120 kDa immunodominant antigen of *Ehrlichia chaffeensis*. The 120-kDa protein is one of the immunodominant proteins of *E. chaffeensis* that stimulates production of specific antibodies in infected humans. Also disclosed are the amino acid sequence of the 120 kDa antigen. Methods of producing a recombinant 120 kDa antigen and therapeutic methods of use of the antigen are also disclosed.

25 Claims, 2 Drawing Sheets

OTHER PUBLICATIONS

Dawson et al., "Susceptibility of White–Tailed Deer (*Odocoileus Virginianus*) to Infection with *Ehrlichia Chaffeensis,* the Etiologic Agent of Human Ehrlichiosis," *J Clin Microbiol,* 32:2725–2728, 1994.

Dumler and Bakken, "Ehrlichial Diseases of Humans: Emerging Tick–Borne Infections," *Clin Infect Dis,* 20:1102–1110, 1995.

Dumler et al., "Identification of Ehrlichia in Human Tissue," *N Engl J Med,* 325:1109–1110, 1991.

Dumler et al., "Isolation and Characterization of a New Strain of *Ehrlichia Chaffeensis* from a Patient with Nearly Fatal Monocytic Ehrlichiosis," *J Clin Microbiol,* 33(7):1704–1711, 1995.

Dumler et al., "Persistent Infection with *Ehrlichia Chaffeensis,*" *Clin Infect Dis,* 17:903–305, 1993.

Dumler et al., "Serologic Cross–Reactions Among *Ehrlichia Equi, Ehrlichia Phagocytophila* and Human Granulocytic Ehrlichia," *Journal of Clinical Microbiology,* 33(5):1098–1103, May 1995.

Dutta et al., "Molecular Cloning and Analysis of Recombinant Major Antigens of *Ehrlichia Risticii,*" *Infection and Immunity,* 59(3):1162–1169, Mar. 1991.

Everett et al., "Human Ehrlichiosis in Adults After Tick Exposure. Diagnosis Using Polymerase Chain Reaction," *Ann Intern Med,* 120:730–735, 1994.

Paparone et al., "Ehrlichiosis with Pancytopenia and ARDS," *N Jersey Med,* 92:381–385, 1995.

Perez et al., "*Ehrlichia Canis*–Like Agent Isolated from a Man in Venezuela: Antigenic and Genetic Characterization," *J Clin Microbiol,* 34:2133–2139, 1996.

Popov et al., "Ultrastructural Variation of Cultured *Ehrlichia Chaffeensis,*" *J Med Microbiol,* 43:411–421, 1995.

Ratnasamy et al., "Central Nervous System Manifestations of Human Ehrlichiosis," *Clin Infect Dis,* 32:314–319, 1996.

Rikihisa, "Cross–Reacting Antigens Between *Neorickettsia Helminthoeca* and Ehrlichia Species, Shown by Immunofluorescence and Western Immunoblotting," *Journal of Clinical Microbiology,* 29(9):2024–2029, Sep. 1991.

Rikihisa et al., "Isolation and Continuous Culture of *Neorickettsia Helminthoeca* in a Macrophage Cell Line," *Journal of Clinical Microbiology,* 29(9):1928–1933, 1991.

Roland et al., "Ehrlichiosis—A Cause of Prolonged Fever," *Clin Infect Dis.,* 20:821–825, 1995.

Shankarappa et al., "Antigenic and Genomic Relatedness Among *Ehrlichia Risticii, Ehrlichia Sennestsu,* and *Ehrlichia Canis,*" *International Journal of Systematic Bacteriology,* 42(1):127–132, Jan. 1992.

Shankarappa et al., "Identification of the Protective 44–Kilodalton Recombinant Antigen of *Ehrlichia Risticii,*" *Infection and Immunity,* 60(2):612–617, Feb. 1992.

Standaert et al., "Ehrlichiosis in a Golf–Oriented Retirement Community," *N Engl Med,* 333:420–425, 1995.

Fichtenbaum et al., "Ehrlichiosis Presenting as a Life–Threatening Illness with Features of the Toxic Shock Syndrome," *Am J Med,* 95:351–357, 1993.

Fishbein et al., "Human Ehrlichiosis: Prospective Acive Surveillance in Febrile Hospitalized Patients," *J Infect Dis,* 160:803–809, 1989.

Harkess et al., "Neurologic Abnormalities in a Patient with Human Ehrlichiosis," *South Med J,* 83:1341–1343, 1990.

Kaylor et al., "Passive Transfer of Antibody to *Ehrlichia Risticii* Protects Mice from Ehrlichiosis," *Infect Immun,* 59:2058–2062, 1991.

Lewis et al., "Effect of Canine Immune Macrophages and Canine Immune Serum on the Growth of *Ehrlichia Canis,*" *Am J Vet Res,* 39:77–82, 1978.

Lewis et al., "Effect of Canine Immune Serum of the Growth of *Ehrlichia Canis* Within Nonimmune Canine Macrophages," *Am J Vet Res,* 39:71–76, 1990.

Maeda et al., "Human Infection with *Ehrlichia Canis,* A Leukocytic Rickettsia," *N Engl J Med,* 316:853–856, 1987.

Messick and Rikihisa, "Presence of Parasite Antigen on the Surface of $P388D_1$ Cells Infected with *Ehrlichia Risticii,*" *Infect. Immun,* 60:3079–3086, 1992.

Morais et al., "First European Case of Ehrlichiosis," *Lancet,* 338:633–634, 1991.

Paddock et al., "Brief Report: Fatal Seronegative Ehrlichiosis in a Patient with HIV Infection," *N Engl J Med,* 329:1164–1167, 1993.

Chen et al (1994) Am. J. Trop. Med. Hyg. 50(1), 52–58.

Wilson et al (1994) Nature 368 (6466), 32–38., Seq. alignment pp. 1–3.

SEQUENCE LISTING

```
(1) GENERAL INFORMATION:

   (iii) NUMBER OF SEQUENCES: 10

(2) INFORMATION FOR SEQ ID NO:1:

     (i) SEQUENCE CHARACTERISTICS:
          (A) LENGTH: 2160 base pairs
          (B) TYPE: nucleic acid
          (C) STRANDEDNESS: single
          (D) TOPOLOGY: linear

    (ix) FEATURE:
          (A) NAME/KEY: CDS
          (B) LOCATION: 171..2054

    (xi) SEQUENCE DESCRIPTION: SEQ ID NO:1:

TGGAGTTGTA GTTAAACTTA TACATCGTAG AGTTAAGTAG TTTGGTTAAT GTTTAGGTAA      60

CATCCTAATA CGTATATGAG CTATCAATTC TATAGAGTAT GTTATTTTAT GATAGAGAAT     120

TGATTGTGGA GTTGGATTTG GCAATACGTT TAAAATTAAA GGAGATTTTT ATG GAT       176
                                                       Met Asp
                                                         1

ATT GAT AAT AGT AAC ATA AGT ACA GCC GAT ATA CGG AGT AAT ACT GAT      224
Ile Asp Asn Ser Asn Ile Ser Thr Ala Asp Ile Arg Ser Asn Thr Asp
          5                  10                  15

GGC TTG ATA GAC ATA ATT ATG CGT ATA TTA GGT TTT GGT AAT AAG AAT      272
Gly Leu Ile Asp Ile Ile Met Arg Ile Leu Gly Phe Gly Asn Lys Asn
     20                  25                  30

ATT GTG CAA CCA CAG GAT CTG GGT TCT GAA ATT TAT CAG CAA GAG CAA      320
Ile Val Gln Pro Gln Asp Leu Gly Ser Glu Ile Tyr Gln Gln Glu Gln
 35                  40                  45                  50

GAA GAT GAC ACA GTC TCT CAA CCT TCA TTA GAG CCA TTT GTT GCA GAA      368
Glu Asp Asp Thr Val Ser Gln Pro Ser Leu Glu Pro Phe Val Ala Glu
                 55                  60                  65

AGT GAA GTT TCT AAA GTT GAA CAA GAA AAA ACT AAC CCT GAG GTT TTA      416
Ser Glu Val Ser Lys Val Glu Gln Glu Lys Thr Asn Pro Glu Val Leu
             70                  75                  80

ATA AAA GAT TTG CAA GAT GTT GCG AGT CAT GAA TCT GGT GTA TCA GAT      464
Ile Lys Asp Leu Gln Asp Val Ala Ser His Glu Ser Gly Val Ser Asp
         85                  90                  95

CAG CCA GCT CAA GTT GTT ACA GAG AGA GAA AAT GAA ATT GAA TCC CAT      512
Gln Pro Ala Gln Val Val Thr Glu Arg Glu Asn Glu Ile Glu Ser His
    100                 105                 110

CAA GGA GAA ACA GAA AAA GAA AGT GGA ATA ACT GAA TCT CAT CAG AAA      560
Gln Gly Glu Thr Glu Lys Glu Ser Gly Ile Thr Glu Ser His Gln Lys
115                 120                 125                 130

GAA GAT GAA ATA GTA TCT CAA TCT TCA TCA GAG CCA TTT GTT GCA GAA      608
Glu Asp Glu Ile Val Ser Gln Ser Ser Ser Glu Pro Phe Val Ala Glu
                135                 140                 145

AGT GAA GTT TCT AAA GTT GAA CAA GAA GAA ACT AAC CCT GAA GTT TTA      656
Ser Glu Val Ser Lys Val Glu Gln Glu Glu Thr Asn Pro Glu Val Leu
            150                 155                 160
```

-continued

```
ATA AAA GAT TTG CAA GAT GTT GCG AGT CAT GAA TCT GGT GTA TCA GAT      704
Ile Lys Asp Leu Gln Asp Val Ala Ser His Glu Ser Gly Val Ser Asp
        165                 170                 175

CAG CCA GCT CAA GTT GTT ACA GAG AGA GAA AGT GAA ATT GAA TCC CAT      752
Gln Pro Ala Gln Val Val Thr Glu Arg Glu Ser Glu Ile Glu Ser His
    180                 185                 190

CAA GGA GAA ACA GAA AAA GAA AGT GGA ATA ACT GAA TCT CAT CAG AAA      800
Gln Gly Glu Thr Glu Lys Glu Ser Gly Ile Thr Glu Ser His Gln Lys
195                 200                 205                 210

GAA GAT GAA ATA GTA TCT CAA CCT TCA TCA GAG CCA TTT GTT GCA GAA      848
Glu Asp Glu Ile Val Ser Gln Pro Ser Ser Glu Pro Phe Val Ala Glu
            215                 220                 225

AGT GAA GTT TCT AAA GTT GAA CAA GAA GAA ACT AAC CCT GAA GTT TTA      896
Ser Glu Val Ser Lys Val Glu Gln Glu Glu Thr Asn Pro Glu Val Leu
            230                 235                 240

ATA AAA GAT TTG CAA GAT GTT GCG AGT CAT GAA TCT GGT GTA TCA GAT      944
Ile Lys Asp Leu Gln Asp Val Ala Ser His Glu Ser Gly Val Ser Asp
        245                 250                 255

CAG CCA GCT CAA GTT GTT ACA GAG AGA GAA AGT GAA ATT GAA TCC CAT      992
Gln Pro Ala Gln Val Val Thr Glu Arg Glu Ser Glu Ile Glu Ser His
    260                 265                 270

CAA GGA GAA ACA GAA AAA GAA AGT GGA ATA ACT GAA TCT CAT CAG AAA     1040
Gln Gly Glu Thr Glu Lys Glu Ser Gly Ile Thr Glu Ser His Gln Lys
275                 280                 285                 290

GAA GAT GAA ATA GTA TCT CAA CCT TCA TCA GAG CCA TTT GTT GCA GAA     1088
Glu Asp Glu Ile Val Ser Gln Pro Ser Ser Glu Pro Phe Val Ala Glu
            295                 300                 305

AGT GAA GTT TCT AAA GTT GAA CAA GAA GAA ACT AAC CCT GAA GTT TTA     1136
Ser Glu Val Ser Lys Val Glu Gln Glu Glu Thr Asn Pro Glu Val Leu
            310                 315                 320

ATA AAA GAT TTG CAA GAT GTT GCG AGT CAT GAA TCT GGT GTA TCA GAT     1184
Ile Lys Asp Leu Gln Asp Val Ala Ser His Glu Ser Gly Val Ser Asp
        325                 330                 335

CAG CCA GCT CAA GTT GTT ACA GAG AGA GAA AGT GAA ATT GAA TCC CAT     1232
Gln Pro Ala Gln Val Val Thr Glu Arg Glu Ser Glu Ile Glu Ser His
    340                 345                 350

CAA GGA GAA ACA GAA AAA GAA AGT GGA ATA ACT GAA TCT CAT CAG AAA     1280
Gln Gly Glu Thr Glu Lys Glu Ser Gly Ile Thr Glu Ser His Gln Lys
355                 360                 365                 370

GAA GAT GAA ATA GTA TCT CAA CCT TCA TCA GAG CCA TTT GTT GCA GAA     1328
Glu Asp Glu Ile Val Ser Gln Pro Ser Ser Glu Pro Phe Val Ala Glu
            375                 380                 385

AGT GAA GTT TCT AAA GTT GAA CAA GAA GAA ACT AAC CCT GAA GTT TTA     1376
Ser Glu Val Ser Lys Val Glu Gln Glu Glu Thr Asn Pro Glu Val Leu
            390                 395                 400

ATA AAA GAT TTG CAA GAT GTT GCG AGT CAT GAA TCT GGT GTA TCA GAT     1424
Ile Lys Asp Leu Gln Asp Val Ala Ser His Glu Ser Gly Val Ser Asp
        405                 410                 415

CAG CCA GCT CAA GTT GTT ACA GAG AGA GAA AGT GAA ATT GAA TCC CAT     1472
Gln Pro Ala Gln Val Val Thr Glu Arg Glu Ser Glu Ile Glu Ser His
    420                 425                 430

CAA GGA GAA ACA GAA AAA GAA AGT GGA ATA ACT GAA TCT CAT CAG AAA     1520
Gln Gly Glu Thr Glu Lys Glu Ser Gly Ile Thr Glu Ser His Gln Lys
435                 440                 445                 450

GAA GAT GAA ATA GTA TCT CAA CCT TCA TCA GAG CCA TTT GTT GCA GAA     1568
Glu Asp Glu Ile Val Ser Gln Pro Ser Ser Glu Pro Phe Val Ala Glu
            455                 460                 465

AGT GAA GTT TCT AAA GTT GAA CAA GAA AAA ACT AAC CCT GAA ATT CTA     1616
Ser Glu Val Ser Lys Val Glu Gln Glu Lys Thr Asn Pro Glu Ile Leu
            470                 475                 480
```

```
GTA GAA GAT TTG CCA TTA GGT CAA GTG ATT CCG GTT GTT GTA GAG AAA      1664
Val Glu Asp Leu Pro Leu Gly Gln Val Ile Pro Val Val Val Glu Lys
        485                 490                 495

GAT GAA ATG TTT GCA CCT TCA TTT AAT CCA ATC GTT ATA AAG GAG GAA      1712
Asp Glu Met Phe Ala Pro Ser Phe Asn Pro Ile Val Ile Lys Glu Glu
    500                 505                 510

GAT AAA GTT TGT GAA ACT TGC GAA CAA GAA TTT GAG ATT GTA AAG GAT      1760
Asp Lys Val Cys Glu Thr Cys Glu Gln Glu Phe Glu Ile Val Lys Asp
515                 520                 525                 530

TCA CAG ACT GTA AAA GGT AGT GAA GAT ATA ATA TCA CCT ATG CAA TGC      1808
Ser Gln Thr Val Lys Gly Ser Glu Asp Ile Ile Ser Pro Met Gln Cys
                535                 540                 545

TTA GAA AGT ATG GAT TCT ATA GTT TCA ACA ATA TTT GAA AGT GGA ATG      1856
Leu Glu Ser Met Asp Ser Ile Val Ser Thr Ile Phe Glu Ser Gly Met
            550                 555                 560

TTA TGT CCT ATG TCA AAA CCT GGA CAG TAT GTT TGT GGG TAT GAA ATG      1904
Leu Cys Pro Met Ser Lys Pro Gly Gln Tyr Val Cys Gly Tyr Glu Met
        565                 570                 575

TAT ATG TAT GGA TTT CAA GAT GTG AAA GAC TTA TTA GGT GGT TTA TTA      1952
Tyr Met Tyr Gly Phe Gln Asp Val Lys Asp Leu Leu Gly Gly Leu Leu
    580                 585                 590

AGT AAT GTT CCT GTG TGT TGT AAT GTT AGC CTT TAT TTT ATG GAA CAT      2000
Ser Asn Val Pro Val Cys Cys Asn Val Ser Leu Tyr Phe Met Glu His
595                 600                 605                 610

AAT TAC TTT ACT AAC CAT GAG AAT ATT AAT CAC AAT GTA GTA AAT GAT      2048
Asn Tyr Phe Thr Asn His Glu Asn Ile Asn His Asn Val Val Asn Asp
                615                 620                 625

ATT GTA TAATTGTAAG GTTTAGTCTT GAGATAGCAA GTGATGCTTT TATTAAGTAT      2104
Ile Val

TGCTTGCTAT TTTTTTGTTT ATTTACCTGC TTTTTATATG GGAGAAATCA TATATT       2160
```

(2) INFORMATION FOR SEQ ID NO:2:

(i) SEQUENCE CHARACTERISTICS:
(A) LENGTH: 628 amino acids
(B) TYPE: amino acid
(D) TOPOLOGY: linear (ii) MOLECULE TYPE: protein (xi) SEQUENCE DESCRIPTION: SEQ ID NO:2:

```
Met Asp Ile Asp Asn Ser Asn Ile Ser Thr Ala Asp Ile Arg Ser Asn
  1               5                  10                  15

Thr Asp Gly Leu Ile Asp Ile Ile Met Arg Ile Leu Gly Phe Gly Asn
             20                  25                  30

Lys Asn Ile Val Gln Pro Gln Asp Leu Gly Ser Glu Ile Tyr Gln Gln
         35                  40                  45

Glu Gln Glu Asp Asp Thr Val Ser Gln Pro Ser Leu Glu Pro Phe Val
     50                  55                  60

Ala Glu Ser Glu Val Ser Lys Val Glu Gln Glu Lys Thr Asn Pro Glu
 65                  70                  75                  80

Val Leu Ile Lys Asp Leu Gln Asp Val Ala Ser His Glu Ser Gly Val
                 85                  90                  95

Ser Asp Gln Pro Ala Gln Val Val Thr Glu Arg Glu Asn Glu Ile Glu
            100                 105                 110

Ser His Gln Gly Glu Thr Glu Lys Glu Ser Gly Ile Thr Glu Ser His
        115                 120                 125

Gln Lys Glu Asp Glu Ile Val Ser Gln Ser Ser Ser Glu Pro Phe Val
    130                 135                 140
```

-continued

```
Ala Glu Ser Glu Val Ser Lys Val Glu Gln Glu Glu Thr Asn Pro Glu
145                 150                 155                 160

Val Leu Ile Lys Asp Leu Gln Asp Val Ala Ser His Glu Ser Gly Val
                165                 170                 175

Ser Asp Gln Pro Ala Gln Val Val Thr Glu Arg Glu Ser Glu Ile Glu
            180                 185                 190

Ser His Gln Gly Glu Thr Glu Lys Glu Ser Gly Ile Thr Glu Ser His
        195                 200                 205

Gln Lys Glu Asp Glu Ile Val Ser Gln Pro Ser Ser Glu Pro Phe Val
    210                 215                 220

Ala Glu Ser Glu Val Ser Lys Val Glu Gln Glu Glu Thr Asn Pro Glu
225                 230                 235                 240

Val Leu Ile Lys Asp Leu Gln Asp Val Ala Ser His Glu Ser Gly Val
                245                 250                 255

Ser Asp Gln Pro Ala Gln Val Val Thr Glu Arg Glu Ser Glu Ile Glu
            260                 265                 270

Ser His Gln Gly Glu Thr Glu Lys Glu Ser Gly Ile Thr Glu Ser His
        275                 280                 285

Gln Lys Glu Asp Glu Ile Val Ser Gln Pro Ser Ser Glu Pro Phe Val
    290                 295                 300

Ala Glu Ser Glu Val Ser Lys Val Glu Gln Glu Glu Thr Asn Pro Glu
305                 310                 315                 320

Val Leu Ile Lys Asp Leu Gln Asp Val Ala Ser His Glu Ser Gly Val
                325                 330                 335

Ser Asp Gln Pro Ala Gln Val Val Thr Glu Arg Glu Ser Glu Ile Glu
            340                 345                 350

Ser His Gln Gly Glu Thr Glu Lys Glu Ser Gly Ile Thr Glu Ser His
        355                 360                 365

Gln Lys Glu Asp Glu Ile Val Ser Gln Pro Ser Ser Glu Pro Phe Val
    370                 375                 380

Ala Glu Ser Glu Val Ser Lys Val Glu Gln Glu Glu Thr Asn Pro Glu
385                 390                 395                 400

Val Leu Ile Lys Asp Leu Gln Asp Val Ala Ser His Glu Ser Gly Val
                405                 410                 415

Ser Asp Gln Pro Ala Gln Val Val Thr Glu Arg Glu Ser Glu Ile Glu
            420                 425                 430

Ser His Gln Gly Glu Thr Glu Lys Glu Ser Gly Ile Thr Glu Ser His
        435                 440                 445

Gln Lys Glu Asp Glu Ile Val Ser Gln Pro Ser Ser Glu Pro Phe Val
    450                 455                 460

Ala Glu Ser Glu Val Ser Lys Val Glu Gln Glu Lys Thr Asn Pro Glu
465                 470                 475                 480

Ile Leu Val Glu Asp Leu Pro Leu Gly Gln Val Ile Pro Val Val Val
                485                 490                 495

Glu Lys Asp Glu Met Phe Ala Pro Ser Phe Asn Pro Ile Val Ile Lys
            500                 505                 510

Glu Glu Asp Lys Val Cys Glu Thr Cys Glu Gln Glu Phe Glu Ile Val
        515                 520                 525

Lys Asp Ser Gln Thr Val Lys Gly Ser Glu Asp Ile Ile Ser Pro Met
    530                 535                 540

Gln Cys Leu Glu Ser Met Asp Ser Ile Val Ser Thr Ile Phe Glu Ser
545                 550                 555                 560

Gly Met Leu Cys Pro Met Ser Lys Pro Gly Gln Tyr Val Cys Gly Tyr
                565                 570                 575
```

-continued

```
Glu Met Tyr Met Tyr Gly Phe Gln Asp Val Lys Asp Leu Leu Gly Gly
            580                 585                 590

Leu Leu Ser Asn Val Pro Val Cys Cys Asn Val Ser Leu Tyr Phe Met
        595                 600                 605

Glu His Asn Tyr Phe Thr Asn His Glu Asn Ile Asn His Asn Val Val
    610                 615                 620

Asn Asp Ile Val
625
```

(2) INFORMATION FOR SEQ ID NO:3:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:3:

GTAATACGAC TACACTATAG GGCTGGCTGA TCT 33

(2) INFORMATION FOR SEQ ID NO:4:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:4:

GAGAATTGAT TGTGGAGTTG G 21

(2) INFORMATION FOR SEQ ID NO:5:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:5:

CATTAGGTCA AGTGATTCCG G 21

(2) INFORMATION FOR SEQ ID NO:6:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:6:

AAATTTCAGA ACCCAGATCC T 21

(2) INFORMATION FOR SEQ ID NO:7:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:7:

ACATAACATT CCACTTTCAA A 21

(2) INFORMATION FOR SEQ ID NO:8:

```
     (i) SEQUENCE CHARACTERISTICS:
          (A) LENGTH: 21 base pairs
          (B) TYPE: nucleic acid
          (C) STRANDEDNESS: single
          (D) TOPOLOGY: linear

    (xi) SEQUENCE DESCRIPTION: SEQ ID NO:8:

AAACAAAAAA ATAGCAAGCA A                                                  21


(2) INFORMATION FOR SEQ ID NO:9:

     (i) SEQUENCE CHARACTERISTICS:
          (A) LENGTH: 1716 base pairs
          (B) TYPE: nucleic acid
          (C) STRANDEDNESS: single
          (D) TOPOLOGY: linear

    (ix) FEATURE:
          (A) NAME/KEY: CDS
          (B) LOCATION: 57..1700

    (xi) SEQUENCE DESCRIPTION: SEQ ID NO:9:

GAGAATTGAT TGTGGAGTTG GATTTGGCAA TACGTTTAAA ATTAAAGGAG ATTTTT         56

ATG GAT ATT GAT AAT AGT AAC ATA AGT ACA GCC GAT ATA CGG AGT AAT      104
Met Asp Ile Asp Asn Ser Asn Ile Ser Thr Ala Asp Ile Arg Ser Asn
  1               5                  10                  15

ACT GAT GGC TTG ATA GAC ATA ATT ATG CGT ATA TTA GGT TTT GGT AAT      152
Thr Asp Gly Leu Ile Asp Ile Ile Met Arg Ile Leu Gly Phe Gly Asn
             20                  25                  30

AAG AAT ATT GTG CAA CCA CAG GAT CTG GGT TCT GAA ATT TAT CAG CAA      200
Lys Asn Ile Val Gln Pro Gln Asp Leu Gly Ser Glu Ile Tyr Gln Gln
         35                  40                  45

GAG CAA GAA GAT GAC ACA GTC TCT CAA CCT TCA TTA GAG CCA TTT GTT      248
Glu Gln Glu Asp Asp Thr Val Ser Gln Pro Ser Leu Glu Pro Phe Val
     50                  55                  60

GCA GAA AGT GAA GTT TCT AAA GTT GAA CAA GAA AAA ACT AAC CCT GAG      296
Ala Glu Ser Glu Val Ser Lys Val Glu Gln Glu Lys Thr Asn Pro Glu
 65                  70                  75                  80

GTT TTA ATA AAA GAT TTG CAA GAT GTT GCG AGT CAT GAA TCT GGT GTA      344
Val Leu Ile Lys Asp Leu Gln Asp Val Ala Ser His Glu Ser Gly Val
                 85                  90                  95

TCA GAT CAG CCA GCT CAA GTT GTT ACA GAA AGA GAA AAT GAA ATT GAA      392
Ser Asp Gln Pro Ala Gln Val Val Thr Glu Arg Glu Asn Glu Ile Glu
            100                 105                 110

TCC CAT CAA GGA GAA ACA GAA AAA GAA AGT GGA ATA ACT GAA TCT CAT      440
Ser His Gln Gly Glu Thr Glu Lys Glu Ser Gly Ile Thr Glu Ser His
        115                 120                 125

CAG AAA GAA GAT GAA ATA GTA TCT CAA CCT TCA TCA GAG CCA TTT GTT      488
Gln Lys Glu Asp Glu Ile Val Ser Gln Pro Ser Ser Glu Pro Phe Val
    130                 135                 140

GCA GAA AGT GAA GTT TCT AAA GTT GAA CAA GAA GAA ACT AAC CCT GAA      536
Ala Glu Ser Glu Val Ser Lys Val Glu Gln Glu Glu Thr Asn Pro Glu
145                 150                 155                 160

GTT TTA ATA AAA GAT TTG CAA GAT GTT GCG AGT CAT GAA TCA GGT GTA      584
Val Leu Ile Lys Asp Leu Gln Asp Val Ala Ser His Glu Ser Gly Val
                165                 170                 175

TCA GAT CAG CCA GCT CAA GTT GTT ACA GAG AGA GAA AGT GAA ATT GAA      632
Ser Asp Gln Pro Ala Gln Val Val Thr Glu Arg Glu Ser Glu Ile Glu
            180                 185                 190

TCC CAT CAA GGA GAA ACA GAA AAA GAA AGT GGA ATA ACT GAA TCT CAT      680
Ser His Gln Gly Glu Thr Glu Lys Glu Ser Gly Ile Thr Glu Ser His
        195                 200                 205
```

-continued

```
CAG AAA GAA GAT GAA ATA GTA TCT CAA TCT TCA TCA GAG CCA TTT GTT       728
Gln Lys Glu Asp Glu Ile Val Ser Gln Ser Ser Ser Glu Pro Phe Val
    210                 215                 220

GCA GAA AGT GAA GTT TCT AAA GTT GAA CAA GAA GAA ACT AAC CCT GAA       776
Ala Glu Ser Glu Val Ser Lys Val Glu Gln Glu Glu Thr Asn Pro Glu
225                 230                 235                 240

GTT TTA ATA AAA GAT TTG CAA GAT GTT GCG AGT CAT GAA TCT GGT GTA       824
Val Leu Ile Lys Asp Leu Gln Asp Val Ala Ser His Glu Ser Gly Val
                245                 250                 255

TCA GAT CAG CCA GCT CAA GTT GTT ACA GAG AGA GAA AGT GAA ATT GAA       872
Ser Asp Gln Pro Ala Gln Val Val Thr Glu Arg Glu Ser Glu Ile Glu
            260                 265                 270

TCC CAT CAA GGA GAA ACA GAA AAA GAA AGT GGA ATA ACT GAA TCT CAT       920
Ser His Gln Gly Glu Thr Glu Lys Glu Ser Gly Ile Thr Glu Ser His
        275                 280                 285

CAG AAA GAA GAT GAG ATA GTA TCT CAA TCT TCA TCA GAG CCA TTT GTT       968
Gln Lys Glu Asp Glu Ile Val Ser Gln Ser Ser Ser Glu Pro Phe Val
    290                 295                 300

GCA GAA AGT GAA GTT TCT AAA GTT GAA CAA GAA GAA ACT AAC CCT GAA      1016
Ala Glu Ser Glu Val Ser Lys Val Glu Gln Glu Glu Thr Asn Pro Glu
305                 310                 315                 320

GTT TTA ATA AAA GAT TTG CAA GAT GTT GCG AGT CAT GAA TCA GGT GTA      1064
Val Leu Ile Lys Asp Leu Gln Asp Val Ala Ser His Glu Ser Gly Val
                325                 330                 335

TCA GAT CAG CCA GCT CAA GTT GTT ACA GAG AGA GAA AGT GAA ATT GAA      1112
Ser Asp Gln Pro Ala Gln Val Val Thr Glu Arg Glu Ser Glu Ile Glu
            340                 345                 350

TCC CAT CAA GGA GAA ACA GAA AAA GAA AGT GGA ATA ACT GAA TCT CAT      1160
Ser His Gln Gly Glu Thr Glu Lys Glu Ser Gly Ile Thr Glu Ser His
        355                 360                 365

CAG AAA GAA GAT GAA ATA GTA TCT CAA CCT TCA TCA GAG CCA TTT GTT      1208
Gln Lys Glu Asp Glu Ile Val Ser Gln Pro Ser Ser Glu Pro Phe Val
    370                 375                 380

GCA GAA AGT GAA GTT TCT AAA GTT GAA CAA GAA AAA ACT AAC CCT GAA      1256
Ala Glu Ser Glu Val Ser Lys Val Glu Gln Glu Lys Thr Asn Pro Glu
385                 390                 395                 400

ATT CTA GTA GAA GAT TTG CCA TTA GGT CAA GTG ATT CCG GTT GTT GTA      1304
Ile Leu Val Glu Asp Leu Pro Leu Gly Gln Val Ile Pro Val Val Val
                405                 410                 415

GAG AAA GAT GAA ATG TTT GCA CCT TCA TTT AAT CCA ATC GTT ATA AAG      1352
Glu Lys Asp Glu Met Phe Ala Pro Ser Phe Asn Pro Ile Val Ile Lys
            420                 425                 430

GAG GAA GAT AAA GTT TGT GAA ACT TGC GAA CAA GAA TTT GAG ATT GTA      1400
Glu Glu Asp Lys Val Cys Glu Thr Cys Glu Gln Glu Phe Glu Ile Val
        435                 440                 445

AAG GAT TCA CAG ACT GTA AAA GGT AGT GAA GAT ATA ATA TCA CCT ATC      1448
Lys Asp Ser Gln Thr Val Lys Gly Ser Glu Asp Ile Ile Ser Pro Ile
    450                 455                 460

GAA TGC TTA GAA AGT ATG GAT TCT ATA GTT TCA ACA ATA TTT GAA AGT      1496
Glu Cys Leu Glu Ser Met Asp Ser Ile Val Ser Thr Ile Phe Glu Ser
465                 470                 475                 480

GGA ATG TTA TGT CCT ATG TCA AAA CCT GGA CAG TAT GTT TGT GGG TAT      1544
Gly Met Leu Cys Pro Met Ser Lys Pro Gly Gln Tyr Val Cys Gly Tyr
                485                 490                 495

GAA ATG TAT ATG TAT GGA TTT CAA GAT GTG AAA GAC TTA TTA GGT GGT      1592
Glu Met Tyr Met Tyr Gly Phe Gln Asp Val Lys Asp Leu Leu Gly Gly
            500                 505                 510

TTA TTA AGT AAT GTT CCT GTG TGT TGT AAT GTT AGC CTT TAT TTT ATG      1640
Leu Leu Ser Asn Val Pro Val Cys Cys Asn Val Ser Leu Tyr Phe Met
        515                 520                 525
```

-continued

```
GAA CAT AAT TAC TTT ACT AAC CAT GAG AAT ATT AAT CAC AAT GTA GTA      1688
Glu His Asn Tyr Phe Thr Asn His Glu Asn Ile Asn His Asn Val Val
    530                 535                 540

AAT GAT ATT GTA TAATTGTAAG GTTTAG                                    1716
Asn Asp Ile Val
545
```

(2) INFORMATION FOR SEQ ID NO:10:

(i) SEQUENCE CHARACTERISTICS:
(A) LENGTH: 548 amino acids
(B) TYPE: amino acid
(D) TOPOLOGY: linear (ii) MOLECULE TYPE: protein (xi) SEQUENCE DESCRIPTION: SEQ ID NO:10:

```
Met Asp Ile Asp Asn Ser Asn Ile Ser Thr Ala Asp Ile Arg Ser Asn
  1               5                  10                  15

Thr Asp Gly Leu Ile Asp Ile Ile Met Arg Ile Leu Gly Phe Gly Asn
             20                  25                  30

Lys Asn Ile Val Gln Pro Gln Asp Leu Gly Ser Glu Ile Tyr Gln Gln
         35                  40                  45

Glu Gln Glu Asp Asp Thr Val Ser Gln Pro Ser Leu Glu Pro Phe Val
     50                  55                  60

Ala Glu Ser Glu Val Ser Lys Val Glu Gln Glu Lys Thr Asn Pro Glu
 65                  70                  75                  80

Val Leu Ile Lys Asp Leu Gln Asp Val Ala Ser His Glu Ser Gly Val
                 85                  90                  95

Ser Asp Gln Pro Ala Gln Val Val Thr Glu Arg Glu Asn Glu Ile Glu
            100                 105                 110

Ser His Gln Gly Glu Thr Glu Lys Glu Ser Gly Ile Thr Glu Ser His
        115                 120                 125

Gln Lys Glu Asp Glu Ile Val Ser Gln Pro Ser Ser Glu Pro Phe Val
    130                 135                 140

Ala Glu Ser Glu Val Ser Lys Val Glu Gln Glu Glu Thr Asn Pro Glu
145                 150                 155                 160

Val Leu Ile Lys Asp Leu Gln Asp Val Ala Ser His Glu Ser Gly Val
                165                 170                 175

Ser Asp Gln Pro Ala Gln Val Val Thr Glu Arg Glu Ser Glu Ile Glu
            180                 185                 190

Ser His Gln Gly Glu Thr Glu Lys Glu Ser Gly Ile Thr Glu Ser His
        195                 200                 205

Gln Lys Glu Asp Glu Ile Val Ser Gln Ser Ser Ser Glu Pro Phe Val
    210                 215                 220

Ala Glu Ser Glu Val Ser Lys Val Glu Gln Glu Glu Thr Asn Pro Glu
225                 230                 235                 240

Val Leu Ile Lys Asp Leu Gln Asp Val Ala Ser His Glu Ser Gly Val
                245                 250                 255

Ser Asp Gln Pro Ala Gln Val Val Thr Glu Arg Glu Ser Glu Ile Glu
            260                 265                 270

Ser His Gln Gly Glu Thr Glu Lys Glu Ser Gly Ile Thr Glu Ser His
        275                 280                 285

Gln Lys Glu Asp Glu Ile Val Ser Gln Ser Ser Ser Glu Pro Phe Val
    290                 295                 300

Ala Glu Ser Glu Val Ser Lys Val Glu Gln Glu Glu Thr Asn Pro Glu
305                 310                 315                 320
```

-continued

```
Val Leu Ile Lys Asp Leu Gln Asp Val Ala Ser His Glu Ser Gly Val
                325                 330                 335

Ser Asp Gln Pro Ala Gln Val Val Thr Glu Arg Glu Ser Glu Ile Glu
            340                 345                 350

Ser His Gln Gly Glu Thr Glu Lys Glu Ser Gly Ile Thr Glu Ser His
        355                 360                 365

Gln Lys Glu Asp Glu Ile Val Ser Gln Pro Ser Ser Glu Pro Phe Val
    370                 375                 380

Ala Glu Ser Glu Val Ser Lys Val Glu Gln Glu Lys Thr Asn Pro Glu
385                 390                 395                 400

Ile Leu Val Glu Asp Leu Pro Leu Gly Gln Val Ile Pro Val Val Val
                405                 410                 415

Glu Lys Asp Glu Met Phe Ala Pro Ser Phe Asn Pro Ile Val Ile Lys
            420                 425                 430

Glu Glu Asp Lys Val Cys Glu Thr Cys Glu Gln Glu Phe Glu Ile Val
        435                 440                 445

Lys Asp Ser Gln Thr Val Lys Gly Ser Glu Asp Ile Ile Ser Pro Ile
    450                 455                 460

Glu Cys Leu Glu Ser Met Asp Ser Ile Val Ser Thr Ile Phe Glu Ser
465                 470                 475                 480

Gly Met Leu Cys Pro Met Ser Lys Pro Gly Gln Tyr Val Cys Gly Tyr
                485                 490                 495

Glu Met Tyr Met Tyr Gly Phe Gln Asp Val Lys Asp Leu Leu Gly Gly
            500                 505                 510

Leu Leu Ser Asn Val Pro Val Cys Cys Asn Val Ser Leu Tyr Phe Met
        515                 520                 525

Glu His Asn Tyr Phe Thr Asn His Glu Asn Ile Asn His Asn Val Val
    530                 535                 540

Asn Asp Ile Val
545
```

IMMUNODOMINANT 120 KDA SURFACE-EXPOSED ADHESION PROTEIN GENES OF *EHRLICHIA CHAFFEENSIS*

FIELD OF THE INVENTION

The present invention relates generally to the field of obligate intracellular parasitic bacteria, particularly agents of rickettsia type diseases and more specifically the ehrlichia tribe of bacteria. This disclosure also encompasses the fields of isolated genes encoding surface antigens of the bacteria and the diagnostic, therapeutic and taxonomic use of such antigens.

BACKGROUND OF THE INVENTION

The government owns rights in the present invention pursuant to grant number AI31431 from the National Institute of Allergy and Infectious Diseases.

Human ehrlichial infections are increasingly recognized in the United States and worldwide. Ehrlichiae are small, pleomorphic, obligately intracellular bacteria which are members of the family Rickettsiaceae (Chen et al., 1994). Hematopoietic cells are the primary targets of ehrlichial infection. Ehrlichiae that cause human disease include the mononuclear phagocyte pathogens *Ehrlichia sennetsu* and *E. chaffeensis* and a granulocytic ehrlichia closely related to *E. phagocytophila* and *E. equi* (Anderson et al., 1991; Chen et al., 1994; Rikihisa, 1991). Human monocytic ehrlichiosis in the United States appears to be caused by *E. chaffeensis* (Anderson et al., 1991; Everett et al., 1994). Human monocytic ehrlichiosis was first reported in the United States in 1987 (Fishbein et al, 1987, Maeda et al, 1987), and the isolation of the causative agent, *Ehrlichia chaffeensis*, from a patient was reported in 1991 (Dawson et al, 1991). The disease has been documented serologically in 30 states of the United States, in Africa, and in Europe (Fishbein et al, 1994, Morais et al, 1991, Uhaa et al, 1992). Human monocytic ehrlichiosis is a moderate to severe illness, even life-threatening in some cases (Fichtenbaum et al, 1993, Paddock et al, 1993, Tal and Shannahan, 1995). Ticks are the most likely vector. Most patients have a history of tick bite or exposure to ticks prior to onset of illness (Fishbein et al, 1994). *E. chaffeensis*-specific DNA sequences have been amplified from ticks (Anderson et al, 1993).

The immunodominant antigens of various ehrlichial species are cross-reactive, making diagnosis of a particular species more difficult. For example, *Ehrlichia chaffeensis* is genetically and antigenically closely related to *E. canis* and *E. ewingii*, canine pathogens, and *E. muris*, a Japanese rodent isolate (Anderson et al, 1992, van Vliet et al, 1992, Wen et al, 1995). One study has shown that rabbit and human *E. chaffeensis* antisera react with more than 20 *E. chaffteensis* antigens ranging from 20 to 200 kDa (Chen et al., 1994). The 120-, 66-, 58-, 44-, 28-, and kDa proteins are the immunodominant antigens of *E. chaffeensis* which react with serum antibodies from persons who have recovered from human monocytic ehrlichiosis (Chen et al, 1994, Dumler et al, 1995). The 22 kDa antigen cross-reacts with *E. canis*. The 66, 64, 55 and 44 kDa proteins cross-react with *E. sennetsu*, and the 55 and 44 kDa antigens cross-react with *E. risticii*, and the major immunodominant antigens, 66, 55 and 44 kDa, cross-reacted with *E. chaffeensis, E. canis, E. sennetsu* and *E. risticii* (Chen et al., 1994). Others have demonstrated serologic cross-reactions among *E. equi, E. phagocytophila* and human granulocytic ehrlichia (Dumler et al., 1995) and cross-reactions among *Neorickettsia helminthoeca* and *E. risticii, E. sennetsu* and *E. canis* (Rikisha, 1991).

A general method for identifying a rickettsial or related organism, including the various Ehrlichial species, is based on the amplification of the 16S rRNA gene. However, this test does not distinguish between species or even strains, some of which are more pathogenic than others. Unfortunately, the immunodominant proteins and their encoding genes, that are specific for each species and that could be used for diagnosis and for the development of vaccines or treatments based on surface antigenicity have not been isolated.

The present invention seeks to overcome this and other deficiencies in the art by providing the first example of an isolated gene that encodes an immunodominant antigen in the human pathogen, *Ehrlichia chaffeensis*. This discovery enables the development of diagnostic techniques, and the production of specific antigens and antibodies to be used in active and passive immunization techniques for preventative and therapeutic applications for both animal and human subjects.

SUMMARY OF THE INVENTION

The present invention may be described in certain embodiments as an isolated nucleic acid segment encoding a 120 kDa immunodominant protein of *Erlichia chaffeensis*, or as an isolated nucleic acid segment that encodes a 120 kDa protein that is immunoreactive with anti-*Ehrlichia chaffeensis* serum. Anti-*Ehrlichia chaffeensis* serum is serum from an animal or a human that has been inoculated or otherwise exposed to *Ehrlichia chaffeensis*, or has recovered from an infection so that the subject's immune system has produced antibodies to the *Ehrlichia chaffeensis* surface antigens. The serum may be obtained from a human who has recovered from an *E. chaffeensis* infection or who is actively infected, or it may be obtained from an animal such as a rabbit, mouse, horse, goat, rat or any other animal that is capable of a humoral immune response and that has been injected or exposed to *E. chaffeensis*.

It is understood that the 120 kDa antigen described herein has an apparent weight of 120 kDa when analyzed by SDS PAGE as disclosed herein, and is not necessarily the predicted molecular weight that is expected from the deduced amino acid sequence. The invention may also be described in certain embodiments as a nucleic acid segment that encodes a protein that has the amino acid sequence disclosed herein as SEQ ID NO:2 or SEQ ID NO:10. It is understood that due to degeneracy in the genetic code and due to the presence of flanking nucleic acid sequences outside the coding region, that many different sequences may encode the amino acid sequence of SEQ ID NO:2 or SEQ ID NO:10, and that all such sequences would be encompassed by the present invention. Particularly preferred however, are nucleic acid segments comprising a contiguous sequence consisting of the sequence or the complement of SEQ ID NO:1 or SEQ ID NO:9.

In addition to the sequences designated herein as SEQ ID NO:1 and SEQ ID NO:2, which are based on the isolated antigen from the Arkansas strain of *Erhlichia chaffeensis*, the same antigen has been isolated from the Sapulpa strain (Dumler et al., 1995). This sequence, for which the nucleic acid sequence is designated SEQ ID NO:9, and the amino acid sequence is designated SEQ ID NO:10, may also be substituted for the sequences of SEQ ID NO:1 and SEQ ID NO:2, respectively. It is also noted that the 120 kDa antigen sequences contain a series of repeats. And that the number of repeats is different for the antigens isolated from the two strains, i.e. there is one more repeat in the Arkansas strain sequences than in the Sapulpa strain sequences. It is contemplated, therefore, that alternate sequences that contain more or fewer repeat sequences would also be useful as diagnostic or therapeutic agents in the practice of the present invention. For example, it is contemplated that one might delete one or more repeat sequences from SEQ ID NO:1, SEQ ID NO:2, SEQ ID NO:9 or SEQ ID NO:10 or that one might insert one or more repeat sequences into those sequences and that such altered sequences would be essentially functionally equivalent to the disclosed sequences.

The nucleic acid segments of the present invention may be operatively linked to a promoter and most preferably to a recombinant promoter. A recombinant promoter is a promoter that is not adjacent the nucleic acid sequences of the present invention in its naturally occurring state, but is operatively linked to the present sequences by genetic manipulation by man. By operatively linked is meant that the promoter sequence is upstream or linked in the 5' direction from the translation start site and directs the binding and initiation of the DNA dependent RNA polymerase reaction into the gene. It is also understood that the nucleic acid sequences claimed herein as a part of the present invention may be DNA or RNA segments.

The present invention may also be described in certain embodiments as a vector comprising a region that encodes the amino acid sequence of SEQ ID NO:2 or SEQ ID NO:10. A preferred vector to be used in the present invention is a lambda phage vector, a plasmid vector, a vaccinia virus or baculovirus. It is also understood that the vector may be an expression vector capable of expressing a peptide or polypeptide encoded by SEQ ID NO:1 or SEQ ID NO:9 in a cell. A preferred expression vector is a pGEX vector. The present invention may even be a host cell comprising a nucleic acid segment encoding the 120 kDa antigen of the present invention. A preferred host cell is an *E. coli* cell. Other cells that may be used in the practice of the invention include *Mycobacterium bovis* (BCG strain) cells.

In certain embodiments, the present invention may be described as a recombinant 120 kDa antigen of *Ehrlichia chaffeensis* or even as a recombinant protein consisting essentially of the amino acid sequence, SEQ ID NO:2 or SEQ ID NO:10, or as a recombinant protein encoded by a nucleic acid segment in accordance with SEQ ID NO:1 or SEQ ID NO:9. It is also an aspect of the invention that the nucleic acid segment may be contained in a vector. In certain embodiments, the antigen will be dispersed in a pharmaceutically acceptable carrier. As used herein, "pharmaceutically acceptable carrier" includes any and all solvents, dispersion media, coatings, antibacterial and antifungal agents, isotonic and absorption delaying agents and the like. The use of such media and agents for pharmaceutical preparations is well known in the art. Except insofar as any conventional media or agent is incompatible with the active ingredient, its use in the therapeutic compositions is contemplated.

In certain embodiments, the present invention may be described as an isolated nucleic acid segment comprising a sequence region that consists of at least a 14, 17, 20, 30, 50, 75, 100, 200 or even a 500 nucleotide long contiguous sequence that has the same sequence as, or is complementary to, a 14, 17, 20, 30, 50, 75, 100, 200 or even a 500 nucleotide long or longer, even up to full length contiguous sequence of SEQ ID NO:1 or SEQ ID NO:9. The isolated nucleic acid segments of the present invention may also be described as comprising a contiguous sequence of at least about 14 bases complementary to a region of SEQ ID NO:1 from base 171 to base 350, and in particular has having the sequence of SEQ ID NO:6. They may also be described as comprising a contiguous sequence of at least about 14 bases complementary to a region of SEQ ID NO:1 from base 1371 to base 1920, and more particularly as having the sequence of SEQ ID NO:7 or SEQ ID NO:8. The segments may further be described as comprising a contiguous sequence of at least about 14 bases corresponding to bases 1 to 371 of SEQ ID NO:1, more particularly a having the sequence of SEQ ID NO:4, or alternatively as comprising a contiguous sequence of at least about 14 bases corresponding to bases 1371 to 1920 of SEQ ID NO:1 and more particularly as having the sequence of SEQ ID NO:5.

An isolated nucleic acid segment comprising an *Ehrlichia chaffeensis* gene promoter region, consisting essentially of bases 129 through 170 of SEQ ID NO:1 is also an aspect of the present invention. The promoter may be operatively linked to the gene encoding the 120 kDa antigen or to another structural gene. The promoter may also be operatively linked to a reporter gene, such as a β-galactosidase gene, a chloramphenicol acyl transferase gene, a luciferase gene or a *Schistosoma japonicum* glutathione-S-transferase gene.

In certain embodiments, the present invention may be described as an antibody immunoreactive with a recombinant 120 kDa antigen as disclosed herein, and preferably as a monoclonal antibody.

A certain aspect of the invention may be described as a method of detecting the presence of *Ehrlichia chaffeensis* comprising the steps of:

obtaining a sample suspected of containing *Ehrlichia chaffeensis,* isolating the genetic material from said sample; and amplifying a portion of said genetic material by use of the PCR;

wherein the PCR primers are selected to hybridize to opposite strands of a double stranded nucleic acid molecule comprising the sequence of SEQ ID NO:1 or SEQ ID NO:9 and its complement, and wherein said hybridization is to the region of SEQ ID NO:1 from base 1 to base 171 or from base 1371 to base 1920, and wherein at least one of said primers hybridizes to a coding region of SEQ ID NO:1 and further wherein the presence of a detectable amplification product is indicative of the presence of *Ehrlichia chaffeensis* in the sample. The polymerase chain reaction (PCR) is a well known technique in the art and is routinely used to amplify genetic sequences as disclosed in U.S. Pat. No. 4,683,202 (incorporated herein by reference). In the practice of the method, the forward PCR primer may comprise a sequence that consists of SEQ ID NO:4 and the reverse PCR primer may comprise a sequence that consists of SEQ ID NO:6, SEQ ID NO:7 or SEQ ID NO:8. Alternatively, the forward PCR primer may comprise a sequence that consists of SEQ ID NO:5 and the reverse PCR primer may comprise a sequence that consists of SEQ ID NO:7 or SEQ ID NO:8. It is understood that a short sequence may be linked to a primer at the 5' end; however, the primer must match the target nucleic acid at its 3' end.

The invention may be described in certain embodiments as a method of inhibiting *Ehrlichia chaffeensis* infection in a subject comprising the steps of:

identifying a subject suspected of being exposed to or infected with *Ehrlichia chaffeensis*; and administering a composition comprising a 120 kDa antigen of *Ehrlichia chaffeensis* in an amount effective to inhibit an *Ehrlichia chaffeensis* infection. The inhibition may occur through any means such as, i.e. the stimulation of the subject's humoral or cellular immune responses, or by other means such as inhibiting the normal function of the 120 kDa antigen, or even competing with the antigen for interaction with some agent in the subject's body. In the practice of the method, the 120 kDa antigen may be a recombinant protein comprising an amino acid sequence of SEQ ID NO:2 or SEQ ID NO:10, and the recombinant protein may be encoded by a gene comprising a sequence according to SEQ ID NO:1 or SEQ ID NO:9.

The present invention may also be described in certain embodiments as a method of producing a recombinant 120 kDa antigen of *Ehrlichia chaffeensis* comprising the steps of:

obtaining a vector that comprises an expression region comprising a sequence encoding the amino acid sequence of SEQ ID NO:2 or SEQ ID NO:10 operatively linked to a promoter;

transfecting said vector into a cell; and culturing said cell under conditions effective for expression of said expression region. This method may further comprise the step of isolating the 120 kDa antigen. The antigen may be isolated by any of a number of means known in the art, such as affinity chromatography, electrophoresis, gel exclusion chromatography, ion exchange, etc.

As used herein the term "complement" is used to define the strand of nucleic acid which will hybridize to the first nucleic acid sequence to form a double stranded molecule under stringent conditions. Stringent conditions are those that allow hybridization between two nucleic acid sequences with a high degree of homology, but precludes hybridization of random sequences. For example, hybridization at low temperature and/or high ionic strength is termed low stringency and hybridization at high temperature and/or low ionic strength is termed high stringency. The temperature and ionic strength of a desired stringency are understood to be applicable to particular probe lengths, to the length and base content of the sequences and to the presence of formamide in the hybridization mixture.

As used herein, the term "engineered" or "recombinant" cell is intended to refer to a cell into which a recombinant gene, such as a gene encoding an *Ehrlichia chaffeensis* antigen has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene. In addition, the recombinant gene may be integrated into the host genome, or it may be contained in a vector, or in a bacterial genome transfected into the host cell.

BRIEF DESCRIPTION OF THE SEQUENCES

SEQ ID NO:1 is a nucleic acid sequence encoding *Erhrlichia chaffeensis*, Arkansas strain 120 kDa antigen.

SEQ ID NO:2 is the amino acid sequence of *Erhlichia chaffeensis*, Arkansas strain 120 kDa antigen.

SEQ ID NO:3 is a deletion primer sequence.

SEQ ID NO:5 corresponds to nucleotides 1390 to 1410 of SEQ ID NO:1.

SEQ ID NO:6 corresponds to the complement of nucleotides 286 to 306 of SEQ ID NO:1.

SEQ ID NO:7 corresponds to the complement of nucleotides 1602 to 1622 of SEQ ID NO:1.

SEQ ID NO:8 corresponds to the complement of nucleotides 1863 to 1884 of SEQ ID NO:1.

SEQ ID NO:9 is a nucleic acid sequence encoding *Erhlichia chaffeensis*, Sapulpa strain 120 dKa antigen.

SEQ ID NO:10 is the amino acid sequence of *Erhlichia chaffeensis*, Sapulpa strain 120 dKa antigen.

DETAILED DESCRIPTION OF THE INVENTION

Figure 1:
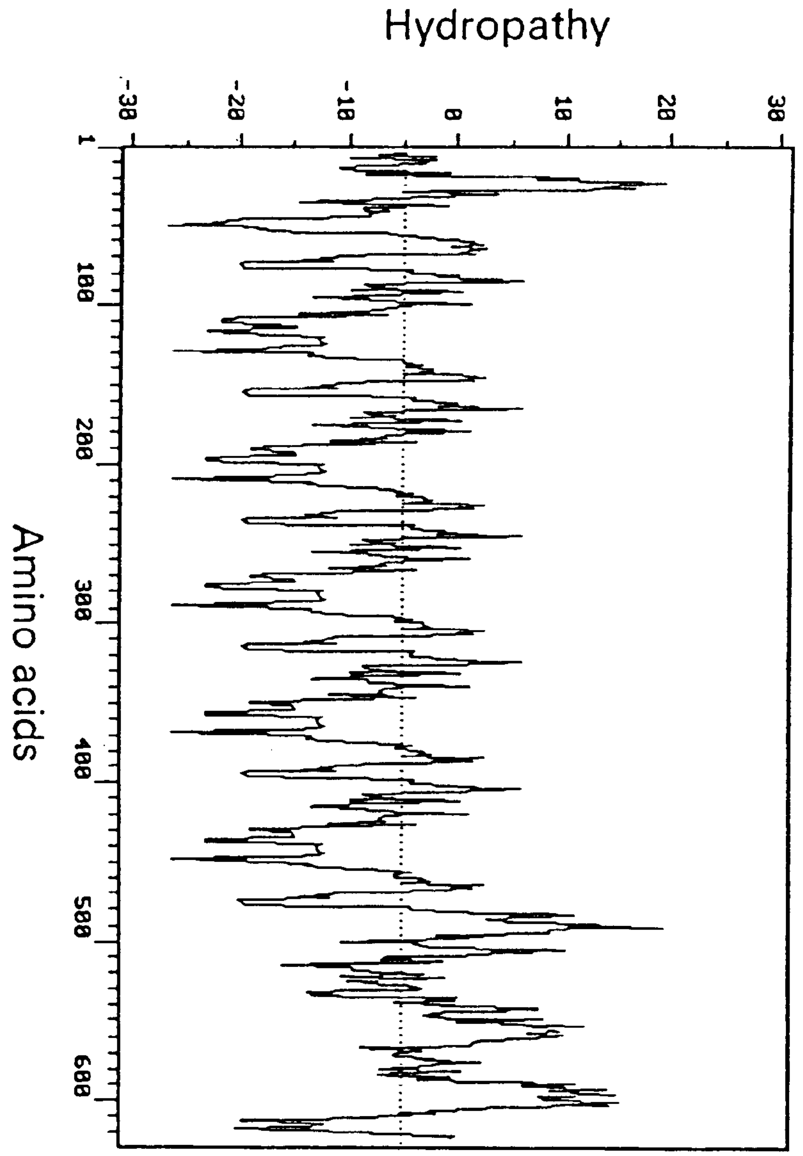
FIG. 1. Hydrophobicity profile of the deduced protein sequence of *E. chaffeensis* 120-kDa protein. The data were calculated using an average group length of 9 amino acids.

The present invention arises from the isolation and the discovery of the amino acid sequences and encoding nucleic acid sequences of the 120 kDa immunodominant antigen of *E. chaffeensis*. The present discovery enables the production of high levels of pure, recombinant antigen. Such antigenic compositions may be used for the production of monoclonal antibodies, for therapeutic administration and for the screening of possible effectors of ehrlichiosis. The nucleic acid segments of the discovery will be useful as hybridization probes and primers for the diagnosis of infection, the identification of related genes, and the amplification of selected sequences, among other well known uses of clinically important gene sequences.

Purification of *E. chaffeensis*

*E. chaffeensis* are purified according to the method described previously (Brouqui et al., 1992). Briefly, *E. chaffeensis*-infected cells are mechanically disrupted, and cell debris removed by centrifugation at 150×g for 10 min. Ehrlichiae in the supernatant are harvested by centrifugation at 7,000×g through a 25% sucrose gradient.

Antibodies

Polyclonal antisera directed against *E. chaffeensis* 120 kDa antigen may preferably be produced in adult New Zealand white rabbits. Rabbits are immunized by simultaneous intramuscular, intradermal, intraperitoneal, and subcutaneous inoculations with a total of 1 mg of protein in Ribi adjuvant (Ribi Immunochem Research Inc., Hamilton, Mont.). Rabbits arc given a booster immunization on day 28 using the same routes and identical immunogen concentration as for the primary immunization and are bled on day 42, at which time the titer is determined by indirect immunoflourescence assay (IFA).

The methods for generating monoclonal antibodies (MAbs) generally begin along the same lines as those for preparing polyclonal antibodies (See, e.g., Antibodies: A Laboratory Manual, Cold Spring Harbor Laboratory, 1988; incorporated herein by reference). Briefly, a polyclonal antibody is prepared by immunizing an animal with an immunogenic composition containing the 120 kDa antigen disclosed herein and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbit is a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-diazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvant and aluminum hydroxide adjuvant.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified 120 kDa *E. chaffeensis* protein. The immunizing composition is administered in a manner effective to stimulate antibody producing cells. Rodents such as mice and rats are preferred animals. The use of rats may provide certain advantages (Goding, 1986, pp. 60–61), but mice may be preferred, with the BALB/c mouse being preferred as this most routinely used and generally gives a higher percentage of stable fusions.

Following immunization, somatic cells with the potential for producing antibodies, specifically B lymphocytes, are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74. 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the medium is supplemented with hypoxanthine.

A selection medium that may be used is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

In a preferred method, eight-week-old female BALB/c mice are immunized with the *E. chaffeensis* 120- kDa antigen. Mice are immunized intraperitoneally three times at 1-week intervals. In the third week after immunization, the mice are boosted by injection into the tail vein. After 72 h, collected splenocytes are fused with SP 2/0 Ag-14 cells with polyethylene glycol (molecular weight, 1,450; Sigma Chemical Co., St. Louis, Mo.) as previously described (Harlow and Lane, 1988).

Indirect immunofluorescence assay (IFA) may be used to screen hybridomas. In brief, the antigens are dotted onto the slides by using a pen and fixed in acetone for 10 min. The antigens are incubated with 20 $\mu$l of hybridoma culture supernatant for 30 min at 37° C. The slides are rinsed once with phosphate-buffered saline (PBS), immersed in PBS for 10 min, and then rinsed with distilled water. The slides are dried and incubated with 20 $\mu$l of fluorescein (dichlorotriazin-amino-fluorescein)-conjugated goat anti-mouse immunoglobulin G (IgG), IgA, and IgM (Jackson Immunoresearch Laboratories, Inc., West Grove, Pa.; diluted 1:100) at 37° C. for 30 min. The slides are washed as described above, dried, mounted with coverslips and examined using a UV light microscope with ×400 magnification Immunodetection Methods In still further embodiments, the present invention concerns immunodetection methods, primarily for detecting the presence of *Ehrlichia chaffeensis*. The antibodies of the present invention may be employed to detect *E. chaffeensis* in a biological sample obtained from a subject and to diagnose such an infection. The steps of various useful immunodetection methods have been described in the scientific literature, and are well known in the art. In general, the detection of immunocomplex formation may be achieved through the application of numerous approaches. These methods are generally based upon the detection of a label or marker, such as any of those radioactive, fluorescent, biological or enzymatic tags or labels known to those in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

Nucleic Acid Hybridization

The nucleic acid sequences disclosed herein will find utility as probes or primers in nucleic acid hybridization embodiments. As such, it is contemplated that oligonucleotide fragments corresponding to the sequence of SEQ ID NO:1 or SEQ ID NO:9 for stretches of between about 15 nucleotides to about 20 or to about 30 nucleotides will find particular utility, with even longer sequences e.g., 40, 50, 100, even up to full length, being more preferred for certain embodiments. The ability of such nucleic acid probes to specifically hybridize to *E. chaffeensis* antigen-encoding sequences will enable them to be of use in a variety of embodiments. For example, the probes can be used in a variety of assays for detecting the presence of complementary sequences in a given sample. However, other uses are envisioned, including the use of the sequence information for the preparation of amplification primers, mutant species primers, or primers for use in preparing other genetic constructions.

The use of a hybridization probe of about 15 nucleotides in length allows the formation of a duplex molecule that is both stable and selective when used to hybridize to a vector such as a plasmid or viral vector. Molecules having complementary sequences over stretches greater than 10 bases in length are generally preferred, though, in order to increase stability and selectivity of the hybrid, and thereby improve the quality and degree of specific hybrid molecules obtained, one will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of *E. chaffeensis* genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and\or high temperature conditions, such as provided by 0.02M–0.15M NaCl at temperatures of 50° C. to 70° C. Such selective conditions tolerate little, if any, mismatch between the probe and the template or target strand.

Of course, for some applications, for example, where one desires to prepare mutants employing a mutant primer strand hybridized to an underlying template or where one seeks to isolate antigen-encoding sequences from related species, functional equivalents, or the like, less stringent hybridization conditions will typically be needed in order to allow formation of the heteroduplex. In these circumstances, one may desire to employ conditions such as 0.1 5M-0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and will generally be a method of choice depending on the desired results.

The tendency for two complementary strands of nucleic acid in solution to anneal or hybridize by forming hydrogen bonds between their complementary bases is critically dependent on the concentration of monovalent or divalent cations in the solution. Sodium ($Na^+$), has been the cation of choice for determining the effects of salt concentration on the stability of duplex nucleic acids. Above a threshold $Na^+$ concentration, two complementary single strands (either DNA or RNA) of nucleic acid will hydrogen bond through interaction of the bases in each strand, to form a double-stranded molecule of DNA, RNA, or even a DNA-RNA heteroduplex. Complementary bases are adenosine and thymidine (in DNA), or adenosine and uridine (in RNA), and cytosine and guanine in both DNA and RNA. Two hydrogen bonds are formed between paired A and T or A and U residues, while C-G base pairing results in the formation of three hydrogen bonds. The G-C base pair is therefore a stronger interaction than the A-U or A-T base pair. In general, hydrogen bonding (leading to duplex formation) does not occur between non-complementary bases. The ability of two single strands to form a stable double-stranded duplex depends on the sequence of bases in each strand being complementary to the other, such that when the strands are aligned in an antiparallel orientation, sequential juxtaposed bases are able to form hydrogen bonds. Although hydrogen bonding between any two complementary bases provides only a weak binding energy, the cumulative binding energy between many sequential paired bases provides sufficient attractive forces to hold the strands together in a stable duplex. Cations enhance the tendency for complementary strands to form hydrogen bonds, by masking the negative charges of the phosphate groups in the phosphodiester linkages which form the “backbone” of the nucleic acid strands. At low concentrations of positively charged ions, repulsive forces between negatively charged strands favor their single-stranded or denatured conformation; as cation concentration is raised, the negative charges are masked, complementary bases pair through hydrogen bonding, and a duplex nucleic acid molecule is formed. In a duplex containing a mismatched (non-complementary) base pair, the single unpaired position in the two otherwise complementary strands provides the target for the single-strand specific RNase in the RNase protection assay.

Other parameters besides cation concentration affect the tendency of complementary strands to exist in the alternative double-stranded or single-stranded conformations. Temperature is a critical variable; as the temperature of a solution of duplex nucleic acid molecules is raised, hydrogen bonds arc broken first in A-U rich regions and finally in G-C rich regions, until above a critical temperature, the complementary strands come apart. The composition of the two strands, i.e., their % GC content, determines the critical temperature for duplex denaturation at a given ionic strength. As a corollary, the % GC also determines the threshold concentration of $Na^+$ needed to maintain duplex stability at a given temperature. Stability of duplex nucleic acid molecules in solution is also affected by the nature of the solvent. For example, duplexes are much less stable in formamide (which destabilizes hydrogen bonds) than in aqueous solution, a fact exploited by molecular biologists to achieve nucleic acid hybridization at lower temperatures than would otherwise be required.

Equations have been derived to relate duplex formation to the major variables of temperature, salt concentration, nucleic acid strand length and composition, and formamide concentration.

E.g.:

$$Tm=81.5-16.6(\log[Na^+])+0.41(\%\ GC)-600/N \quad 1$$

(Tm=temperature for duplex to half denature; N=chain length $$Tm=81.5-16.6(\log[Na^+]+0.41(\%\ GC)-0.63(\%\ formamide)-600/N2$$

One can thus predict whether complementary strands will exist in double-stranded or single-stranded form under a given set of conditions.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates are known which can be employed to provide a means, visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000 or 3,000 being preferred and segments of about 1,000 base pairs in length being particularly preferred.

Hybridization probes may be selected from any portion of any of the sequences disclosed herein. All that is required is to review the sequence set forth in SEQ ID NO:1 or SEQ ID NO:9 and to select any continuous portion of the sequence, from about 10 nucleotides in length up to and including the full length sequence, that one wishes to utilize as a probe or primer. The choice of probe and primer sequences may be governed by various factors, such as, by way of example only, one may wish to employ primers from towards the termini of the total sequence, or primers that flank or include sequences that encode the repeat sequences of SEQ ID NO:2 or SEQ ID NO:10.

The process of selecting and preparing a nucleic acid segment which includes a sequence from within SEQ ID NO:1 or SEQ ID NO:9 may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR technology of U.S. Pat. No. 4,603,102 (incorporated herein by reference), by introducing selected sequences into recombinant vectors for recombinant production, and by other recombinant DNA techniques generally known to those of skill in the art of molecular biology.

Pharmaceutical Compositions

As used herein, “pharmaceutically acceptable carrier” includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. Aqueous compositions (inocula) of the present invention comprise an effective amount of the 120 kDa antigen dissolved or dispersed in a pharmaceutically acceptable aqueous medium. Such compositions are also referred to as inocula.

The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Cloning the 120-kDa protein gene of *E. chaffeensis*

*Ehrlichia chaffeensis* was cultivated in DH82 cells (Wellman et al., 1988; Rikihisha et al., 1991; dawson et al. 1991) and purified by renografin density gradient centrifugation. *E. chaffeensis*, Arkansas strain is preferably grown in DH82 cells, a canine macrophage cell line. Infected cells are cultured in 20 150-$cm^2$ plastic tissue culture flasks with Eagle's minimum essential medium containing 10% fetal calf serum and 4 mM L-glutamine at 37° C. in an atmosphere of 5% $CO_2$. The intracellular growth of the organism is monitored with Romanowsky staining (LeukoStat™; Fisher Scientific, Pittsburgh, Pa.) of cytocentrifuged preparations. The cells are harvested and purified when they are 100% infected. *E. chaffeensis* genomic DNA was partially digested with Xba I and cloned into λ ZAP II phage vector (Stratagene, La Jolla, Calif.). The non-amplified library was screened for ehrlichial antigen production by reaction of IPTG-induced recombinant clones with canine anti-*E. chaffeensis* serum. Five recombinant phage clones reacting with canine anti-*E. chaffeensis* serum were identified and converted into plasmids by in vivo excision according to the instructions of the manufacturer. A 6.5 kb DNA fragment was released from all five recombinant plasmids by Xba I with complete digestion. DNA inserts from all five clones hybridized with digoxigenin-labeled insert DNA of clone pλ5. Therefore, the five clones contained an identical insert, and only clone λ5 and its phagemid derivative, pλ5, were used for subsequent study. The cloned insert in pλ5 hybridized with a 6.5 kb DNA fragment of *E. chaffeensis* DNA digested with Xba I . However, no DNA hybridization was observed between the pλ5 insert and the DH82 cellular DNA. The insert DNA from pλ5 was excised by Xba I digestion and labeled with digoxigenin-11-dUTP (Boehringer Mannheim, Indianapolis, Ind.) using a Dig DNA labeling and detection kit. Three μg of *Ehrlichia chaffeensis* DNA or DH82 cell DNA was digested completely with Xba I, separated electrophoretically in a 1% agarose gel, and transferred onto a nitrocellulose membrane for Southern blotting. DNA hybridization was performed at 60° C.

The *E. coli*-expressed recombinant *E. chaffeensis* protein was identified by Western immunoblotting. pλ5 phage affinity-purified monospecific canine anti-*E. chaffeensis* antibodies reacted with a protein of *E. chaffeensis* with a molecular size of 1 20-kDa. Monospecific canine anti-*E. chaffeensis* 120-kDa protein antibodies were prepared by affinity-purification of canine anti-*E.chaffeensis* serum by λ5 phage lysate. λ5 phage lysate of *E. coli* was prepared by infection of *E. coli* (strain XL1-blue MRF') with λ5 phage. The phage-infected *E. coli* was plated onto LB plates. When the plaques were visible, nitrocellulose membranes soaked in IPTG were placed on the plates to absorb the lysate overnight at 37° C. After blocking with 5% nonfat milk, the membranes were reacted with *E. coli* pre-absorbed canine anti-*E. chaffeensis* serum. The bound antibodies were eluted from antigen on the membrane with 0.2 M glycine (pH 2.8) and concentrated by centrifugation using Centriprep-100 (Amicon, Inc., Beverly, Mass.). Mouse antisera to the recombinant protein were prepared by intraperitoneal injection of the lysate of IPTG-induced *E. coli* expressing the 120-kDa protein of *E. chaffeensis* clone λ5 three times at one week intervals. Proteins were separated electrophoretically in a 10% SDS-polyacrylamide gel and were transferred onto a nitrocellulose membrane. The 120 kDa protein was not detected by non-recombinant λZAP phage affinity-purified antibodies derived from the same canine anti-*E. chaffeensis* serum. Mouse antiserum to *E. coli* containing pλ5 reacted with the 120-kDa protein of *E. chaffeensis* and a 120-kDa protein in the lysate of *E. coli* containing pλ5. However, this serum did not react with any protein with a molecular weight of 120-kDa in the controls, *E. coli* containing only the vector plasmid and DH82 cells. These results demonstrated that the 120-kDa protein expressed by *E. coli* was encoded by an *E. chaffeensis* gene. IPTG induction had no effect on the production of the *E. coli*-expressed 120-kDa protein encoded by pλ5. The result suggested that the *E. coli*-expressed *E. chaffeensis* protein was not a β-galactosidase fusion protein.

Deletion of pλ5 Insert DNA

A 2.3 kb DNA fragment at the 3' end of the insert DNA in pλ5 was deleted by Acc I digestion to form pXA. A 1.4 kb DNA fragment was deleted from the 5' end of the insert DNA in pXA by Xba I and Cla I double digestions to form pCA. pCA contained the minimum insert DNA to express the 120 kDa protein of *E. chaffeensis*. The 120-kDa protein gene of *E. chaffeensis* consisted of 4 tandem repeat units which are too long to sequence by primer walking. Therefore, the repeat region was deleted by a set of timed or genetically engineered deletions. The 5' end of the sense strand of the repeat region was deleted using the Erase-a-Base system (Promega, Madison, Wis.). The insert DNA from the 5' end of the antisense strand could not be deleted by using exonuclease III due to the lack of an appropriate endonuclease enzyme cutting site. After the sequence of the sense strand was determined, the 3' end of the sense strand of the repeat region was deleted by oligonucleotide primer-directed deletion using the Quantum leap nested deletion kit (Clontech Laboratories, Inc., Palo Alto, Calif.) with the deletion primer (5'-GTAATACGACTACACTATAGGGCTGGCTGATCT-3', SEQ ID NO:3). The primer consisted of a 22-mer anchoring domain on the 5' end and a 10 mer 3' tail. The anchoring domain is complementary to the sequence of pBluescript SK(−), adjacent to the insert targeted for deletion. The 3' tail is complementary to the sequence of the last 10 nucleotides of the sense strand of each repeat unit. When the anchoring domains of the primer were annealed to the template DNA, the 3' tail would randomly anneal to each of the repeat units. The new strand was synthesized from the 3' end of the primer with T4 DNA polymerase and was ligated using T4 ligase. In the new strand of DNA, the sequence between two annealed segments of the primer would be looped out and deleted. The plasmids were digested by Sal I. The parental plasmid pCA contained a unique Sal I restriction site which lay between the two domains of the deletion primer. The Sal I restriction site was looped out and deleted in the mutated plasmids. The Sal I digested plasmids were transformed into *E. coli*. The linearized plasmid DNA transforms *E. coli* less efficiently than the circularized plasmid. Therefore the mutated plasmids were selected by restriction enzyme digestion.

Sequence Analysis of the 120-kDa Protein Gene

DNA sequences outside of the repeat region on both strands of the 120-kDa protein gene were determined by primer walking the insert DNA in pλ5, pXA, and pCA. The sequence of the repeat region was obtained by unidirectional deletion of both strands of the repeat region. The sequence of the 120-kDa protein gene of *E. chaffeensis* revealed an 1644 bp open reading frame between nucleotides 171 and 1814. Four 240 nucleotide tandem repeat units were present in the open reading frame from nucleotides 351 to 1310. A sequence identical to the first part of the repeat unit followed the fourth repeat unit from nucleotides 1311 to 1370. The tandem repeat region comprised 60% of the entire gene of the 120-kDa protein of *E. chaffeensis*. Aside from the first repeat unit, all the other repeat units are identical. In the first repeat unit, there are four nucleotides that are different from the corresponding nucleotides in the other repeat units. All the differences are nucleotide substitutions. At the amino acid level, three amino acids of the first repeat unit were different from the others (Table 1). There were two in-frame putative ATG start codons in the beginning of the open reading frame. The first ATG at nucleotide 99 was preceded by a termination codon (TAG) in the same reading frame at position 93. The second ATG was located at nucleotide 171. It seemed likely that the second ATG serves as the translation initiator codon because the consensus sequences of a ribosome binding site (RBS) and a putative *E. coli* promoter were found upstream of this codon, and there were no such sequences upstream of the first ATG codon. The ehrlichial promoter was analyzed based on the consensus sequence of the *E. coli* promoter (Staden, 1984). The putative −35 region (GAGTTG) lies between nucleotides 129 and 134, and the putative −10 region (TTTAAA) spans nucleotides 149 to 154. The space between the −35 and −10 promoter sequences is 14 nucleotides, within the limits of the *E. coli* promoter. The putative RBS (AGGAGA) at nucleotides 160 to 165 was found just 4 nucleotides preceding the ATG start codon. A terminator codon (TAA) was located at nucleotide 1815 and numerous stop codons appeared in the same reading frame in the sequence after the first stop codon. No inverted repeat which could serve as transcription terminator was found downstream of the stop codon. In addition to the sequence of the open reading frame, a 1.4 kb DNA fragment upstream and a 2 kb DNA fragment downstream of the open reading frame were sequenced. A 5' end truncated 400 nucleotide long open reading frame was found upstream of the open reading frame of the 120-kDa gene in the same reading frame. The distance between two open reading frames is 1 kb, and there are numerous stop codons between the two open reading frames. The truncated open reading frame encoded a 19-kDa β-galactosidase fusion protein, and the protein yielded no reaction with either canine or rabbit anti-*E. chaffeensis* sera. No open reading frame was found downstream of the 120-kDa protein gene. DNA sequencing was performed by the dideoxy chain termination procedure using the ds DNA cycle sequence system (GIBCO BRL, Gaithersburg, Md.). The primer was 4' end-labeled with [$\gamma^{32}P$] ATP (Amersham Life Sciences, Arlington Heights, Ill.) using T4 polynucleotide kinase. DNA was synthesized using Taq polymerase in a DNA thermal cycler (Perkin-Elmer Cetus, Norwalk, Conn.).

TABLE I

Mutated nucleotides and amino acids in the first repeat unit in the 120 kDa protein gene of *E. chaffeensis*.

| Position[a] | 46 | 60 | 146 | 232 |
|---|---|---|---|---|
| Repeat unit 1 | A(K[b]) | G(E) | A(N) | T(S) |
| Repeat units 2–5 | G(E) | A(E) | G(S) | C(P) |

[a]:nucleotide position was counted from the first nucleotide of each repeat
[b]:Amino acid.

Similarity Searching.

The NCBI Blast algorithm (D version 1.4) program was used to search sequence similarity of the deduced amino acids of *E. chaffeensis* 120 kDa protein gene (Karlin and Altschul, 1990, and 1993). No significant similarity was found between the *E. chaffeensis* protein sequence and any known protein sequences in the databases.

Hydropathy Analysis of the *E. chaffeensis* 120-kDa Protein

Hydropathy analysis of the deduced amino acid sequence showed that the repeat domain is highly hydrophilic (FIG. 1). Computer analysis of the amino acid sequence using the method of Klein, Kanehisa, and Delisi classified the protein as peripheral (Klein et al, 1985, Kyte and Doolittle, 1982). This information suggests the possibility that the 120-kDa protein is located on the surface of *E. chaffeensis*.

The molecular mass of the protein deduced from the DNA sequence is only 80-kDa. It is substantially smaller than the observed electrophoretic mobility of the protein, which is consistent with a molecular weight of 120-kDa. To evaluate the accuracy of the molecular size of the protein encoded by the gene, the smaller plasmids derived from pλ5 by subcloning and deletion procedures were used. pCA1 was constructed from pCA by endonuclease III deletion. pCA1 contained only a 2.4 kb DNA insert, which included the entire open reading frame of the 120-kDa protein. The whole insert DNA in pCA1 is estimated to encode only a peptide of no more than 90-kDa as calculated on the basis of 1 kb of DNA encoding 37-kDa of protein. However, the pCA1 -encoded recombinant protein has an observed molecular size of 120-kDa. The protein encoded by pCA1 is a β-galactosidase fusion protein. In the fusion protein, the peptide encoded by a part of the β-galactosidase gene consists of only 18 amino acids, less than 5-kDa. Therefore, the discrepancy between the size of the open reading frame and the observed molecular weight of the 120-kDa protein of *E. chaffeensis* is caused by modification of the protein after translation rather than an error in the sequence determination.

Figure 2:
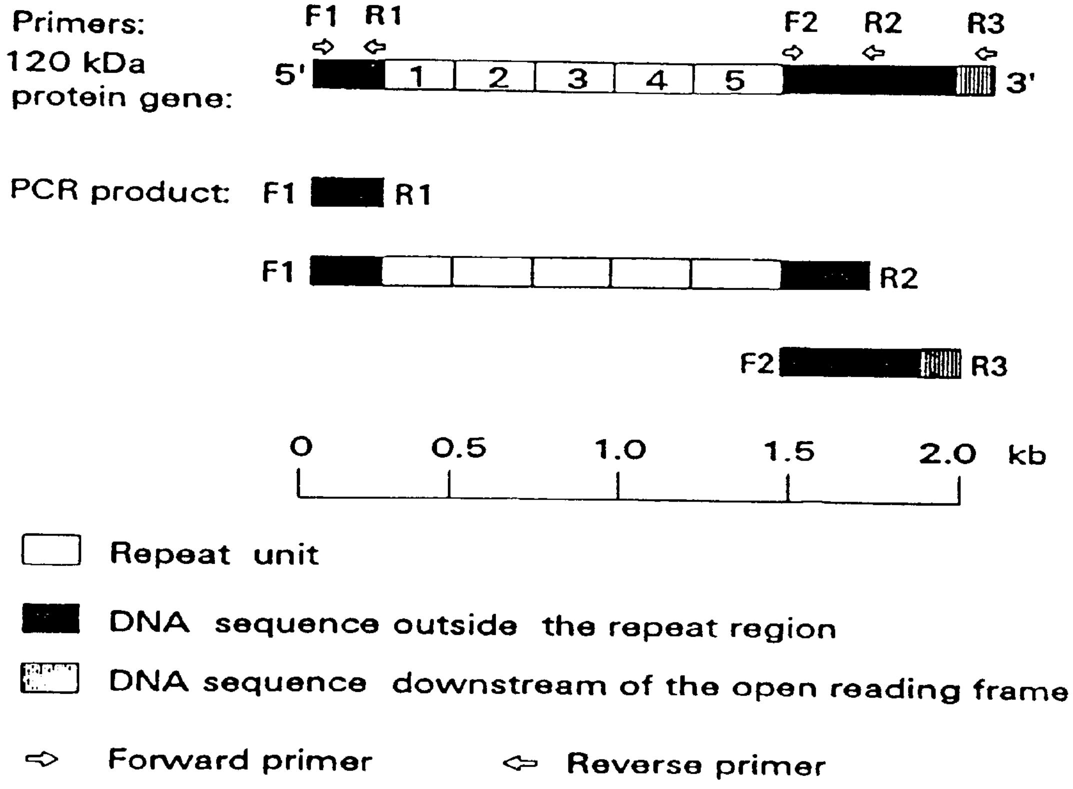
FIG. 2. Diagram of the 120-kDa protein gene of *E. chaffeensis* illustrating the locations and directions of the primers derived from this gene and their PCR products.

PCR Amplification of the 120 kDa Protein Gene in the Members of the Genus Ehrlichia Three primer pairs representing segments of the entire open reading frame of the *E. chaffeensis* 120-kDa protein gene were used to amplify 120 kDa protein genes in other species of Ehrlichia. PCR amplification was performed in a DNA thermal cycler. The PCR program consists of 5 min at 95° C., followed by 30 cycles consisting of melting for 30s at 94° C., annealing for 1 min at 52° C., and DNA synthesis extension for 2 min at 72° C. and a final extension cycle of 3 min at 72° C. The PCR product was analyzed by electrophoresis in a 1% agarose gel. The forward primers F1(5'-GAGAATTGATTGTGGAGTTGG-3', SEQ ID NO:4) and F2(5'-CATTAGGTCAAGTGATTCCGG-3', SEQ ID NO:5) corresponded to nucleotides 115 to 135 and 1390 to 1410, respectively, on the sense strand. The reverse primers R1 (5'-AAATTTCAGAACCCAGATCCT-3', SEQ ID NO:6), R2(5'-ACATAACATTCCACTTTCAAA-3, SEQ ID NO:7), and R3(5'-AAACAAAAA AATAGCAAGCAA-3', SEQ ID NO:8) corresponded to nucleotides 306 to 286, 1622 to 1602, and 1884 to 1862, respectively, on the antisense strand. Primer pair F1-R1 amplified a DNA fragment of 191 bp immediately upstream of the repeat region of the 120-kDa protein gene of *E. chaffeensis*. Primer pair F1-F2 amplified a DNA fragment of 1747 bp including the DNA on both sides of the repeat region and the repeat region. Primer pair F2-R3 amplified a DNA fragment of 494 bp immediately downstream of the repeat region (FIG. 2). The DNA fragments with expected sizes of 191 bp, 1747 bp, and 494 bp were amplified from *E. chaffeensis* Arkansas and 91HE17 strains by using the primer pairs, F1-R1, F1-R2, and F2-R3, respectively. PCR amplification of *E. chaffeensis* DNA with the primer pair F1-R2 produced a ladder with 5 bands. The largest fragment with the molecular weight of 1.7 kb is the dominant product. The incremental difference in sizes of the adjacent bands in the ladder is 240 bp. Therefore, the number of the bands in the ladder corresponded to the number of repeat units, and the size of the bands corresponded to increments of additional repeat units. The DNA of *E. risticii* or *E. canis* was not amplified by PCR using the 120-kDa primers, using *E. risticii* and *E. canis* DNA templates that were readily amplified by 16S rDNA primers. These results suggested that the primer pairs are *E. chaffeensis* species-specific and that the DNA sequences of the *E. canis* 120-kDa protein may diverge substantially from those of *E. chaffeensis*. These apparently species-specific primer pairs could prove useful in the clinical diagnosis of *E. chaffeensis* infection and in epidemiologic investigations of the distribution of *E. chaffeensis* in vector and reservoir hosts.

EXAMPLE 2

Use of the 120 kDa Antigen as a Vaccine

Because antibody appears to play a role in immunity to ehrlichiae by opsonization of surface exposed antigens and enhanced ehrlichial killing after ehrlichial phagocytosis by macrophages, the 120-kDa protein is contemplated to be useful for stimulating protective immunity to *E. chaffeensis* (Kaylor et al, 1991, Lewis and Ristic, 1978, Lewis et al, 1990). The role of T-lymphocyte reactivity to the 120-kDa protein may also prove to be useful as a response to vaccination since expression of as yet unidentified ehrlichial antigens on the host cell is a potential target for cytotoxic T-lymphocytes and antibody-dependent cellular cytotoxicity (Messick and Rikihisa, 1992). This report of what appears to be the first ehrlichial surface protein to have been cloned substantially expands our ability to address those issues.

Aqueous compositions (inocula) of the present invention comprise an effective amount of the 120 kDa antigen dissolved or dispersed in a pharmaceutically acceptable aqueous medium. Such compositions are also referred to as inocula.

The phrase "pharmaceutically acceptable" refers to molecular entities and compositions that do not produce an allergic or similar untoward reaction when administered to a human.

The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A protein may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

As is well known in the art, a given polypeptide may vary in its immunogenicity. It is often necessary therefore to couple the immunogen (e.g., a polypeptide of the present invention) with a carrier. Exemplary and preferred carriers are keyhole limpet hemocyanin (KLH) and human serum albumin. Other carriers may include a variety of lymphokines and adjuvants such as IL2, IL4, IL8 and others.

Means for conjugating a polypeptide to a carrier protein are well known in the art and include glutaraldehyde, m-maleimidobenzoyl-N-hydroxysuccinimide ester carbodiimide and bis-biazotized benzidine. It is also understood that the peptide may be conjugated to a protein by genetic engineering techniques that are well known in the art.

As is also well known in the art, immunogenicity to a particular immunogen can be enhanced by the use of non-specific stimulators of the immune response known as adjuvants. Exemplary and preferred adjuvants include complete BCG, Detox, (RIBI, Immunochem Research Inc.) ISCOMS and aluminum hydroxide adjuvant (Superphos, Biosector).

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables, either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the invention. More specifically, it will be apparent that certain agents which are both chemically and physically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Anderson, B. E., Greene, C. E., Jones, D. C., and Dawson, J. E.: *Ehrlichia ewingii* sp. nov., the etiologic agent of canine granulocytic ehrlichiosis. Int. J. Syst. Bacteriol. 42 (1992) 299–302.

Anderson, B. E., Sims, K. G., Olson, J. G., Childs, J. E., Piesman, J. E., Happ, C. M., Maupin, G. O., and Johnson, B. J. B.: *Amblyomma americanum*: a potential vector of human ehrlichiosis. Am. J. Trop. Med. Hyg. 49 (1993) 239–244.

Campbell, in Monoclonal Antibody Technology, Laboratory Techniques in Biochemistry and Molecular Biology Vol. 13, Burden and Von Knippenberg, Eds. pp. 75–83, Amsterdam, Elseview, 1984

Chen, S-M., Dumler, J. S., Feng, H-M., and Walker, D. H.: Identification of the antigenic constituents of *Ehrlichia chaffeensis*. Am. J. Trop. Med. Hyg. 50 (1994) 52–58.

Dawson, J. E., Anderson, B. E., Fishbein, D. B., Sanchez, J. I,., Goldsmith, C. S., Wilson, K. H., and Duntley, C. W.: Isolation and characterization of an Ehrlichia sp. from a patient diagnosed with human ehrlichiosis. J. Clin. Microbiol. 29 (1991) 2741–2745.

Dumler, J. S., Chen, S-M., Asanovich, K., Trigiani, E., Popov, V. L., and Walker, D. H.: Isolation and characterization of a new strain of *Ehrlichia chaffeensis* from a patient with nearly fatal monocytic ehrlichiosis. J. Clin. Microbiol. 33 (1995) 1704–1711.

Fichtenbaum, C. J., Peterson, L. R., and Weil, G. J.: Ehrlichiosis presenting as a life-threatening illness with features of the toxic shock syndrome. Am. J. Med. 95 (1993) 351–357.

Fishbein, D. B., Sawyer, L. A., Holland, C. J., Hayes, E. B., Okoranyanwu, W., Williams, D., Sikes, R. K., Ristic, M., and McDade, J. E.: Unexplained febrile illness after exposure to ticks: infection with an Ehrlichia? JAMA. 257 (1987) 3100–3104.

Fishbein, D. B., Dawson, J. E., and Robinson, L. E.: Human ehrlichiosis in the United States, 1985 to 1990. Ann. Intern. Med. 120 (1994) 736–743.

Gefter et al., Somatic Cell Genet. 3:231–236 (1977)

Goding, 1986, in Monoclonal Antibodies: Principles and Practice, 2d ed., Orlando, Fla., Academic Press, 1986, pp. 60–61, 65–66, 71–74.

Karlin, S., and Altschul, S. F.: Applications and statistics for multiple high scoring segments in molecular sequences. Proc. Natl. Acad. Sci. USA. 90 (1993) 5873–5877.

Kaylor, P. S., Crawford, T. B., McElwain, T. F., and Palmer, G. H.: Passive transfer of antibody to *Ehrlichia risticii* protects mice from ehrlichiosis. Infect. Immun. 59 (1991) 2058–2062.

Klein, P., Kanehisa, M., and DeLisi, C.: The detection and classification of membrane-spanning proteins. Biochim. Biophys. Acta. 815 (1985) 468–476.

Kohler and Milstein, Nature 256:495–497 (1975)

Kohler and Milstein, Eur. J. Immunol. 6:511–519 (1976) Karlin, S., and Altschul, S. F.: Methods for assessing the statistical significance of molecular sequence features by using general scoring schemes. Proc. Natl. Acad. Sci. USA. 87 (1990) 2264–2268.

Kyte, J., and Doolittle, R. F.: A simple method for displaying the hydropathic character of a protein. J. Mol.Biol. 157 (1982) 105–132.

Lewis, G. E., Jr., and Ristic, M.: Effect of canine immune macrophages and canine immune serum on the growth of *Ehrlichia canis*. Am. J. Vet. Res. 39 (1978) 77–82.

Lewis, G. E., Jr., Hill, S. L., and Ristic, M.: Effect of canine immune serum of the growth of *Ehrlichia canis* within nonimmune canine macrophages. Am. J. Vet. Res. 39 (1990) 71–76.

Maeda, K., Markowitz, N., Hawley, R. C., Ristic, M., Cox, D., and McDade, J. E.: Human infection with *Ehrlichia canis*, a leukocytic rickettsia. N. Engl. J. Med. 316 (1987) 853–856.

Messick, J. B., and Rikihisa, Y.: Presence of parasite antigen on the surface of $P388D_1$ cells infected with *Ehrlichia risticii*. Infect. Immun. 60 (1992) 3079–3086.

Morais, J. D., Dawson, J. E., Greene, C., Filipe, A. R., Galhardas, L. C., and Bacellar, F.: First European case of ehrlichiosis. Lancet 338 (1991) 633–634.

Paddock, C. D., D. P. Suchard, K. L. Grumbach, W. K. Hadley, R. L. Kerschmann, N. W. Abbey, J. E. Dawson, B. E. Anderson, Sims, K. G., Dumler, J. S., and Herndier, B. G.: Brief report: fatal seronegative ehrlichiosis in a patient with HIV infection. N. Engl. J. Med. 329 (1993) 1164–1167.

Rikihisa, Y., Stills, H. and Zimmerman, G. Isolation and continuous culture of Neorickettsia helminthoeca in a macrophage cell line. Journal of Clinical Microbiology, 29(9)(1991:1928–33.

Staden, R.: Computer methods to locate signals in nucleic acid sequences. Nucleic Acids Res. 12 (1994) 505–519.

Tal, A., and Shannahan, D. : Ehrlichiosis presenting as a life-threatening illness. Am. J. Med. 98 (1995) 318–319. (Letter).

Uhaa, I. J., Maclean, J. D., Greene, C. R., and Fishbein, D. B.: A case of human ehrlichiosis acquired in Mali: clinical and laboratory findings. Am. J. Trop. Med. Hyg. 46 (1992) 161–164.

Van Vliet, A. H. M., Jongejan, F., Van Der Zeijst, B. A. M.: Phylogenetic position of *Cowdria ruminantium* (Rickettsiales) determined by analysis of amplified 16S ribosomal DNA sequences. Int. J. Syst. Bacteriol. 42 (1992) 494–498.

Wellman, M. L., Krakowka, S., Jacobs, R. M. and Kociba, G. J. A macrophage-monocyte cell line from a dog with malignant histiocytosis. In Vitro Cellular & Developmental Biology 24 (3)(1988):223–9.

Wen, B., Rikihisa, Y., Mott, J., Fuerst, P. A., Kawahara, M., and Suto, C.: *Ehrlichia muris* sp. nov., identified on the basis of 16S rRNA base sequences and serological, morphological, and biological characteristics. Int. J. Syst. Bacteriol. 45(1995)250–254.

What is claimed is:

1. An isolated nucleic acid segment encoding a 120 kDa protein, wherein said protein is immunoreactive with anti-*Ehrlichia chaffeensis* serum, and wherein said protein has an amino acid sequence of SEQ ID NO:2 or SEQ ID NO:10.

2. The nucleic acid segment of claim 1, comprising a contiguous sequence consisting of the sequence of SEQ ID NO:1 or SEQ ID NO:9 or the full length complement therof.

3. The nucleic acid segment of claim 1 operatively linked to a promoter.

4. The nucleic acid segment of claim 3, wherein said promoter is a recombinant promoter.

5. The nucleic acid segment of claim 1 wherein said nuclueic acid is a DNA segment.

6. A vector comprising a contiguous sequence consisting of the nucleic acid segment of claim 1.

7. The vector of claim 6, wherein said vector is a lambda phage vector.

8. The vector of claim 6, wherein said vector is an expression vector capable of expressing a peptide or polypeptide encoded by SEQ ID NO:1 or SEQ ID NO:9 when said expression vector is introduced into a cell.

9. A host cell comprising the nucleic acid segment of claim 1.

10. The host cell of claim 9, wherein said host cell is a canine macrophage cell.

11. An isolated nucleic acid segment of from 30 to about 100 nucleotides in length, wherein said segment comprises a contiguous sequence region that consists of at least a 30 nucleotide contiguous sequence of SEQ ID NO:1 or SEQ ID NO:9 or the full-length complement thereof.

12. The isolated nucleic acid segment of claim 11, wherein said segment comprises a contiguous full-length sequence of at least 30 bases fully complementary to a region of SEQ ID NO:1 from base 171 to base 350.

13. The isolated nucleic acid segment of claim 12, wherein said segment has the sequence of SEQ ID NO:6.

14. The isolated nucleic acid segment of claim 13, wherein said segment comprises a contiguous full-length sequence of at least 30 bases complementary to a region of SEQ ID NO:1 base 1370 to base 1884.

15. The isolated nucleic acid segment of claim 14, wherein said segment has the sequence of SEQ ID NO:7.

16. The isolated nucleic acid segment of claim 14, wherein said segment has the sequence of SEQ ID NO:8.

17. The isolated nucleic acid segment of claim 11, wherein said segment comprises a contiguous sequence of at least 30 bases corresponding to bases 1 to 371 of SEQ ID NO:1.

18. The isolated nucleic acid segment of claim 17, wherein said segment has the sequence of SEQ ID NO:4.

19. The isolated nucleic acid segment of claim 11, wherein said segment comprises a contiguous sequence of at least 30 bases corresponding to bases 1371 to 1884 of SEQ ID NO:1.

20. The isolated nucleic acid segment of claim 19, wherein said segment has the sequence of SEQ ID NO:5.

21. An isolated nucleic acid segment comprising an *Ehrlichia chaffeensis* gene promoter region, wherein said promoter region includes bases 129 through 170 of SEQ ID NO:1.

22. The isolated nucleic acid segment of claim 21, wherein said promoter is operatively linked to a reporter gene.

23. The isolated nucleic acid segment of claim 22, wherein said reporter gene is a β-galactosidase gene, a chloramphenicol acyl transferase gene, a luciferace gene or a glutathione-S-transferase gene.

24. A method of producing a recombinant 120 kDa antigen of *Ehrlichia chaffeensis* comprising the steps of:

obtaining a vector that comprises an expression region comprising a sequence encoding the amino acid sequence of SEQ ID NO:2 or SEQ ID NO:10 operatively linked to a promoter;

transfecting said vector into a cell; and culturing said cell under conditions effective for expression of said expression region.

25. The method of claim 24, further comprising the step of isolating said 120 kDa antigen.

* * * * *

UNITED STATES PATENT AND TRADEMARK OFFICE

CERTIFICATE OF CORRECTION

PATENT NO. : 6,015,691
DATED : January 18, 2000
INVENTOR(S) : Xue-Jie Yu, et al

It is certified that error appears in the above-identified patent and that said Letters Patent is hereby corrected as shown below:

In Column 1, line 30, "et al," should read --et al.,--.

In Column 1, line 36, "et al," should read --et al.,--.

In Column 1, line 38, "et al," should read --et al.,--.

In Column 1, line 39, "et al," should read --et al.,--.

In Column 1, line 42, "et al," should read --et al.,--.

In Column 1, line 43, "et al," should read --et al.,--.

In Column 1, line 49, "et al," should read --et al.,--.

In Column 1, line 50, "et al," should read --et al.,--.

In Column 1, line 56, "et al," should read --et al.,--.

In Column 1, line 57, "et al," should read --et al.,--.

In Column 2, line 2, "organism" should read --organisms--.

In Column 2, line 7, "genes" should read --gene--.

In Column 2, line 15, please delete the comma after the word "techniques".

UNITED STATES PATENT AND TRADEMARK OFFICE

CERTIFICATE OF CORRECTION

PATENT NO. : 6,015,691
DATED : January 18, 2000
INVENTOR(S) : Xue-Jie Yu, et al

It is certified that error appears in the above-identified patent and that said Letters Patent is hereby corrected as shown below:

In Column 2, line 67, please insert a comma after "i.e.".

In Column 4, line 66, please insert a comma after "i.e.".

In Column 7, line 64, "pp. 71-74. 1986)." should read --pp. 71-74 (1986)--.

In Column 8, line 53, "120- kDA" should read --120-kDA--.

In Column 10, line 8, "and\or" should read --and/or--.

In Column 11, lines 30-35 should read as follows:

--E.g.:

1. $Tm=81.5-16.6(\log[Na^+])+0.4(\%\ GC)-600/N$

2. $Tm-81.5-16.6(\log[Na^+]+0.4(\%\ GC)-0.63(\%formamide)-600/n2$ (Tm=temperature for duplex to half denature; N=chain length--

UNITED STATES PATENT AND TRADEMARK OFFICE

CERTIFICATE OF CORRECTION

PATENT NO. : 6,015,691
DATED : January 18, 2000
INVENTOR(S) : Xue-Jie Yu, et al

It is certified that error appears in the above-identified patent and that said Letters Patent is hereby corrected as shown below:

In Column 13, line 35, "dawson" should read --Dawson--.

In Column 13, line 37, please insert a comma after the word "strain".

In Column 16, under Table 1, line 21, "2-5" should read --2--.

In Column 16, in the first footnote under Table 1, line 23, "nucleotide" should read --Nucleotide--.

In Column 16, in the first footnote under Table 1, line 23, please delete the period after the word "repeat".

In Column 16, line 25, please delete the period after "Searching."

In Column 16, line 29, please delete the comma after "1990,".

UNITED STATES PATENT AND TRADEMARK OFFICE

CERTIFICATE OF CORRECTION

PATENT NO. : 6,015,691
DATED : January 18, 2000
INVENTOR(S) : Xue-Jie Yu, et al

It is certified that error appears in the above-identified patent and that said Letters Patent is hereby corrected as shown below:

In Column 16, line 37, "et al," should read --et al.,--.

In Column 17, line 54, "et al," should read --et al.,--.

In Column 18, line 38, please insert a comma after "see".

In Column 20, line 23, please remove the indentation before "Karlin".

Signed and Sealed this

Twenty-fourth Day of April, 2001

Attest:

NICHOLAS P. GODICI

Attesting Officer

*Acting Director of the United States Patent and Trademark Office*